(12) United States Patent
Isobe et al.

(10) Patent No.: US 9,615,836 B2
(45) Date of Patent: Apr. 11, 2017

(54) REMOTE-CONTROLLED ACTUATOR ASSEMBLY

(75) Inventors: Hiroshi Isobe, Iwata (JP); Takayoshi Ozaki, Iwata (JP)

(73) Assignee: NTN CORPORATION, Osaka (JP)

( * ) Notice: Subject to any disclaimer, the term of this patent is extended or adjusted under 35 U.S.C. 154(b) by 985 days.

(21) Appl. No.: 13/517,448

(22) PCT Filed: Dec. 20, 2010

(86) PCT No.: PCT/JP2010/072874
§ 371 (c)(1),
(2), (4) Date: Jun. 20, 2012

(87) PCT Pub. No.: WO2011/078110
PCT Pub. Date: Jun. 30, 2011

(65) Prior Publication Data
US 2012/0255750 A1 Oct. 11, 2012

(30) Foreign Application Priority Data

Dec. 24, 2009 (JP) ................ 2009-291862

(51) Int. Cl.
*A61B 17/00* (2006.01)
*A61B 17/16* (2006.01)
*B23B 39/14* (2006.01)

(52) U.S. Cl.
CPC ...... *A61B 17/1631* (2013.01); *A61B 17/1633* (2013.01); *A61B 17/1626* (2013.01); *A61B 2017/00327* (2013.01); *B23B 39/14* (2013.01)

(58) Field of Classification Search
CPC ............. A61B 17/068; A61B 17/072; A61B 17/07207; A61B 17/1622; A61B 17/1624;
(Continued)

(56) References Cited

U.S. PATENT DOCUMENTS 4,265,231 A 5/1981 Scheller, Jr. et al.
4,466,429 A 8/1984 Loscher et al.
(Continued)

FOREIGN PATENT DOCUMENTS

EP 2 361 563 A1 8/2011
EP 2 364 652 A1 9/2011
(Continued)

OTHER PUBLICATIONS

International Preliminary Report on Patentability issued Aug. 23, 2012 in corresponding International Patent Application No. PCT/JP2010/072874.

(Continued)

*Primary Examiner* — Stephen F Gerrity
*Assistant Examiner* — Joshua Kotis

(57) ABSTRACT

A remote-controlled actuator assembly includes a distal end member fitted to a tip end of a spindle guide section for alteration in attitude, a tool rotatably provided in the distal end member, a tool rotation drive source for rotating the tool, and an attitude altering drive mechanism for operating the attitude of the distal end member. The spindle guide section has a rotary shaft for transmitting a rotation of the tool rotation drive source to the spindle and an attitude altering member to alter the attitude of the distal end member. The attitude altering mechanism includes an attitude altering drive source, a reduction unit to reduce a speed of input rotation from the attitude altering drive source, a motion converter mechanism to convert a rotational output from the reduction unit to advancing/retracting motion, and an output member to cause the attitude altering member to advance/retract according to an output of the motion converter mechanism.

4 Claims, 17 Drawing Sheets

(58) Field of Classification Search
CPC ............ A61B 17/1626; A61B 17/1631; A61B 17/1633; A61B 2017/2727; A61B 2017/2929; A61B 2034/305; A61B 2034/306; B25J 17/02; B23B 39/14; B23B 45/00; B23B 45/005
USPC ........ 227/175.1, 176.1, 178.1, 179.1; 173/39
See application file for complete search history.

(56) References Cited

U.S. PATENT DOCUMENTS

| | | | | |
|---|---|---|---|---|
| 5,405,344 | A | * | 4/1995 | Williamson et al. ............. 606/1 |
| 5,485,952 | A | * | 1/1996 | Fontayne .................. 227/178.1 |
| 5,547,117 | A | * | 8/1996 | Hamblin ............. A61B 17/072 227/175.2 |
| 5,607,095 | A | * | 3/1997 | Smith ................ A61B 17/0682 227/176.1 |
| 5,616,117 | A | * | 4/1997 | Dinkler ............. A61B 17/0206 600/210 |
| 5,662,662 | A | * | 9/1997 | Bishop ............... A61B 17/0684 227/175.1 |
| 5,695,513 | A | * | 12/1997 | Johnson et al. ............. 606/180 |
| 5,762,458 | A | * | 6/1998 | Wang et al. ...................... 414/1 |
| 6,331,181 | B1 | * | 12/2001 | Tierney et al. ............... 606/130 |
| 7,922,720 | B2 | * | 4/2011 | May et al. ...................... 606/80 |
| 2005/0165420 | A1 | * | 7/2005 | Cha .................... A61B 17/1671 606/150 |
| 2006/0041268 | A1 | * | 2/2006 | Shores ............... A61B 17/1633 606/180 |
| 2006/0229624 | A1 | * | 10/2006 | May et al. ...................... 606/79 |
| 2007/0093810 | A1 | * | 4/2007 | Sartor et al. ..................... 606/42 |
| 2007/0093840 | A1 | | 4/2007 | Pacelli et al. |
| 2007/0265653 | A1 | | 11/2007 | Suzuki |
| 2009/0001129 | A1 | * | 1/2009 | Marczyk .............. A61B 17/072 227/179.1 |
| 2009/0101692 | A1 | * | 4/2009 | Whitman et al. .......... 227/175.1 |
| 2009/0143642 | A1 | * | 6/2009 | Takahashi et al. ........... 600/106 |
| 2010/0012702 | A1 | * | 1/2010 | Marczyk .......... A61B 17/07207 227/175.1 |
| 2010/0193567 | A1 | * | 8/2010 | Scheib ............. A61B 17/07207 227/176.1 |

FOREIGN PATENT DOCUMENTS

| | | |
|---|---|---|
| JP | 58-80213 | 5/1983 |
| JP | 7-163574 | 6/1995 |
| JP | 2001-17446 | 1/2001 |
| JP | 2005-528159 | 9/2005 |
| JP | 2007-301149 | 11/2007 |
| JP | 2009-131374 | 6/2009 |
| WO | WO 03/101308 | 12/2003 |

OTHER PUBLICATIONS

Japanese Office Action mailed Dec. 24, 2013 in corresponding Japanese Patent Application No. 2009-291862.
International Search Report of Corresponding PCT Application PCT/JP2010/072874 mailed Feb. 1, 2011.
Extended and Supplementary European Search Report dated Apr. 22, 2015 in corresponding European Patent Application No. 10839340.6.
International Search Report issued Aug. 23, 2012 in corresponding International Patent Application No. PCT/JP2010/072874.
Communication pursuant of Article 94(3) EPC dated Mar. 9, 2016 in corresponding European Patent Application No. 10 839 340.6.

* cited by examiner

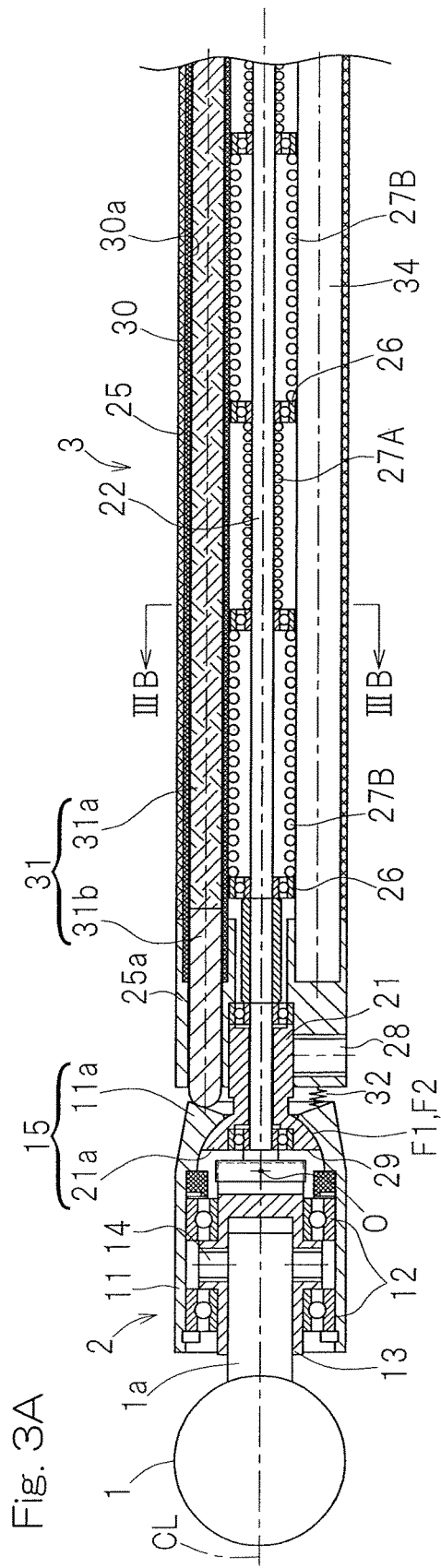
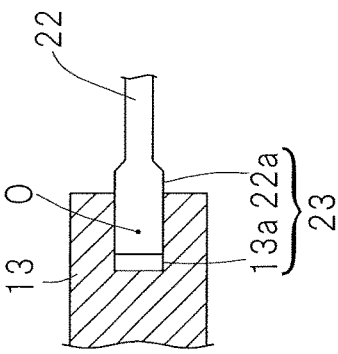
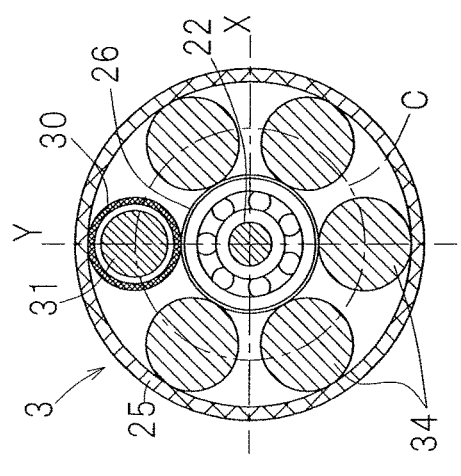
Fig. 3A
Fig. 3B
Fig. 3C

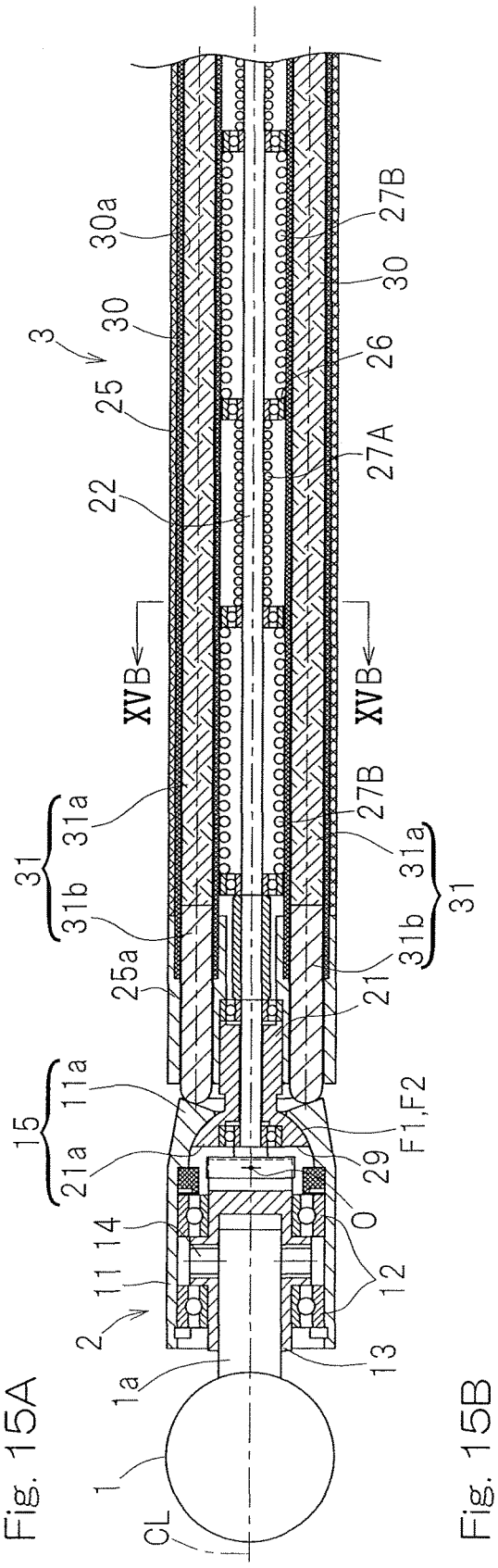
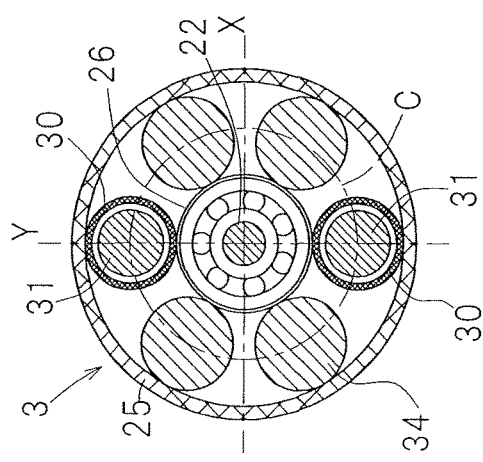
Fig. 15A
Fig. 15B

REMOTE-CONTROLLED ACTUATOR ASSEMBLY

CROSS REFERENCE TO RELATED APPLICATIONS

This application is a national phase application, under 35 U.S.C. 371, of international application No. PCT/JP2010/072874, filed on Dec. 20, 2010, which claimed priority to Japanese Patent Application No. 2009-291862, filed on Dec. 24, 2009, the disclosures of which are incorporated herein by reference.

FIELD OF THE INVENTION

The present invention relates to a remote controlled actuator assembly for use in medical and machine processing fields and capable of changing the attitude of a machine tool.

BACKGROUND ART

Remote controlled actuator assemblies are currently available; some are used in the medical field for osteal treatment and some are used in the mechanical processing field for drilling and cutting. Any of those remote controlled actuator assemblies controls by remote control a machine tool fitted to a distal end of an elongated pipe of a linear or curved configuration. However, since the conventional remote controlled actuator assembly is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator assembly will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet this desire, the following technique has hitherto been suggested. For example, the Patent Document 2 listed below discloses the elongated pipe having its intermediate portion curved twice to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated by 180°.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-017446

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever shape the pipe takes, the working range of the tool is limited by the shape of the pipe and, therefore, it is difficult to process the artificial joint insertion hole so that the living bone and the artificial joint may have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator assembly of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations.

It is to be noted that in the case of the medical actuator having no elongated pipe used therein, a portion where the tool is mounted can change its attitude relative to a portion to be gripped by hand (See, for example, Patent Document 4 listed above.), but nothing has yet been suggested in the art that the attitude of the tool can be altered by remote control.

SUMMARY OF THE INVENTION

An object of the present invention is to provide a remote controlled actuator assembly of a type having an overall compact configuration, in which the attitude of the tool coupled to the tip of the elongated pipe section can be surely and accurately changed by remote control and in which a spindle guide section as the pipe section can be altered in its attitude even if in a curved condition.

A remote controlled actuator assembly of the present invention includes a spindle guide section of an elongated shape, a distal end member fitted to a tip end of the spindle guide section through a distal end member connecting unit for alteration in attitude, a tool rotatably provided in the distal end member, a tool rotation drive source for rotating the tool, and an attitude altering drive source for operating the attitude of the distal end member. The distal end member rotatably supports a spindle for holding the tool, and the spindle guide section has its interior accommodating a rotary shaft for transmitting a rotation of the tool rotation drive source to the spindle and a guide hole having its opposite ends opening. In such a case a flexible attitude altering member is reciprocally movably inserted within the guide hole, and has a tip of the attitude altering member for undergoing a reciprocating or retracting motion in contact with the distal end member so as to alter the attitude of the distal end member about an axis perpendicular to a longitudinal axis of the spindle, the attitude altering member being selectively advanced or retracted by the attitude altering drive source. The attitude altering drive source includes a rotary actuator, and the rotary actuator includes a reduction unit configured to reduce a speed of input rotation from the attitude altering drive source and then to output it; a motion converter mechanism configured to convert a rotational output from the reduction unit to advance or retraction motion and then to output it; and an output member having a contact portion that contacts the base end of the attitude altering member. The contact portion is operable to advance or retract according to an output of the motion converter mechanism, thereby, in turn, causing the attitude altering member to advance or retract. The term "advance or retraction motion" encompasses, in addition to a linear back-and-forth motion, a swing motion.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided at a position distant from the distal end member and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately. Also, since the attitude altering member is flexible, the attitude altering operation takes place assuredly even when the spindle guide section is of a type having a curved portion.

Rotation of the attitude altering drive source, through the reduction unit that reduces the speed of that rotation, is converted by the motion converter mechanism to advance or retraction motion for transmission to the output member. This results in advance or retraction of the output member. The advance or retraction of the output member is transmitted via the contact portion to the base end of the attitude altering member, causing the attitude altering member to advance or retract. With the provision of the reduction unit, even a possibly low output torque from the attitude altering drive source can generate a large torque at an output of the reduction unit thereby to impart a great acting force on the output member. This ensures that the advance or retraction of the attitude altering member is carried out, thereby enhancing the positioning accuracy of the tool mounted to the distal end member. The provision of the reduction unit also leads to reduction in size of the attitude altering drive source, thereby making a remote controlled actuator assembly compact as a whole. In particular, as the attitude altering drive source, a rotary actuator is used together with a combination of the reduction unit, the motion converter mechanism and the output member, with the motion converter mechanism converting the rotational output from the reduction unit to advance or retraction motion and causing via the output member the attitude altering member to advance or retract. Accordingly, the reduction in size of the remote controlled actuator assembly as a whole can be realized.

In the present invention, the motion converter mechanism may include a linear motion mechanism configured to convert the rotational output from the reduction unit to a linear back-and-forth motion, and the linear motion mechanism may include a final output stage forming the aforementioned output member. For example, the linear motion mechanism may include a mechanism employing a screw mechanism or a mechanism that includes a rack and a pinion in mesh with each other. With the provision of the motion converter mechanism that includes the linear motion mechanism, rotation of the attitude altering drive source, which includes the rotary actuator, can cause the attitude altering member to advance or retract. Also, the configuration of the linear motion mechanism including the final output stage and the final output stage forming the output member can make the number of components smaller, thereby resulting in a simplified construction.

The motion converter mechanism may include a linear motion mechanical section configured to convert the rotational output from the reduction unit to a linear back-and-forth motion and a lever mechanical section configured to amplify an output of the linear motion mechanical section for output of an amplified force. In such case the lever mechanical section may include a final output stage forming the aforementioned output member. According to this structural feature, the linear motion mechanical section converts the rotation of the attitude altering drive source, which includes the rotary actuator, to the linear back-and-forth motion, which, in turn, causes the advance or retraction of the attitude altering member. Furthermore, not only does the reduction unit amplify the torque from the attitude altering drive source but also the lever mechanical section amplifies the output of the linear motion mechanical section for output of an amplified force. This results in the advance or retraction motion of the attitude altering member that has a great acting force. The provision of the lever mechanical section allows for use of a reduction unit with a small reduction ratio, thereby achieving reduction in both size and weight of the reduction unit. Also, the configuration of the lever mechanical section including the final output stage and the final output stage forming the aforementioned output member can achieve reduction in the number of components.

In the present invention, when the reduction unit includes an input shaft to which rotation is input from the attitude altering drive source and an output shaft that outputs rotation with a reduced speed, the input and output shafts may be aligned with a common axis or may be perpendicular to each other. For example, where the input and output shafts are aligned with a common axis, a harmonic drive unit or a planetary gear unit may be employed as the reduction unit. These units can achieve a great reduction ratio, in spite of their compact constructions. In the case of the reduction unit including input and output shafts that are perpendicular to each other, design freedom can be enhanced as the attitude altering drive source does not have to be located on an extension line of the output shaft of the reduction unit.

In the present invention, the reduction unit may include a worm that is rotated by rotation of the attitude altering drive source and a worm wheel that is in mesh with the worm. In such case the worm wheel may form the aforementioned output member having a contact portion that slidingly contacts the attitude altering member and is operable to cause the attitude altering member to advance or retract. The configuration of the reduction unit including the combination of the worm and the worm wheel is equivalent to the reduction unit equipped with a motion converter capability. In other words, this results in a unit integrating a reduction mechanism and a motion converter mechanism together, thereby reducing the size of the group of components serving speed reduction and motion conversion functions. Also, a reduction unit that includes the worm and worm wheel can achieve a great reduction ratio. Furthermore, the configuration of the worm wheel forming the aforementioned output member can achieve reduction in the number of components.

In the present invention, the remote controlled actuator assembly may include a drive unit housing to which the base end of the spindle guide section connects, with the drive unit housing containing the reduction unit and the attitude altering drive source being provided outside of the drive unit housing, and a flexible wire configured to transmit rotation of the attitude altering drive source to the reduction unit. The provision of the attitude altering drive source outside of the drive unit housing eliminates the need to dispose electronic components, such as a motor, inside of the drive unit housing. This facilitates sterilization and cleaning of the drive unit housing when the remote controlled actuator assembly is used as a medical instrument. The configuration of the flexible wire transmitting the rotation of the attitude altering drive source provided outside of the drive unit housing to the reduction unit in the drive unit housing results in versatility in terms of a positional relationship between the drive unit housing and the attitude altering drive source provided outside of the drive unit housing, thus enhancing the maneuverability of the remote controlled actuator assembly. Also, the configuration of the reduction unit being downstream of the flexible wire in the path of transmission of rotation can reduce, on the output side of the reduction unit, a rotational phase offset that may be caused by twisting of the flexible wire. Hence, the twisting of the flexible wire does not affect the output member, thereby allowing for precise advance or retraction of the attitude altering member.

In the present invention, the remote controlled actuator assembly may include a power transmission member arranged between the reduction unit and the attitude altering member, and a position detector operable to detect an operational position of the power transmission member. The advance or retraction position of the attitude altering member can be estimated based on the operational position of the power transmission member that is detected by the position detector. The information with regard to the advance or retraction position of the attitude altering member which is estimated in this way can be used to control the attitude altering drive source. The provision of the position detector associated with the power transmission member arranged between the reduction unit and the attitude altering member can prevent a rotational phase offset between the output and the input of the reduction unit that may be caused by, for example, backlash, from undesirably affecting the detection accuracy of the position detector. This allows for precise estimation of the advance or retraction position of the attitude altering member at all times, thereby enhancing the positioning accuracy of the distal end member. Furthermore, this allows for use of a relatively inexpensive reduction unit, thereby achieving reduction of the cost of the remote controlled actuator assembly. Even when a material used for the power transmission member arranged between the reduction unit and the attitude altering member is subject to torsion, the effect of the torsion of that power transmission member can be minimized by the action of the reduction unit. This allows the position detector to perform detection with fine resolving power, thereby enhancing the positioning accuracy of the distal end member.

In the present invention, the spindle guide section may include a curve portion. The configuration of the attitude altering member being flexible enables the attitude altering member to advance or retract in the guide hole, regardless of the presence of the curve portion in the spindle guide section.

BRIEF DESCRIPTION OF THE DRAWINGS

In any event, the present invention will become more clearly understood from the following description of embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the different figures, and:

FIG. 3A shows a longitudinal cross sectional view of a distal end member and a spindle guide section of the remote controlled actuator assembly of FIG. 1;

FIG. 3B shows a cross sectional view of FIG. 3A taken along the line IIIB-IIIB;

FIG. 3C shows a longitudinal cross sectional view of a coupling configuration between the distal end member and a rotary shaft;

FIG. 15A shows a longitudinal cross sectional view of a distal end member and a spindle guide section of a remote controlled actuator assembly according to the first variant which differs in the system for altering the distal end member;

FIG. 15B shows a cross sectional view of FIG. 15A taken along the line XVB-XVB;

DESCRIPTION OF PREFERRED EMBODIMENTS

Figure 1:
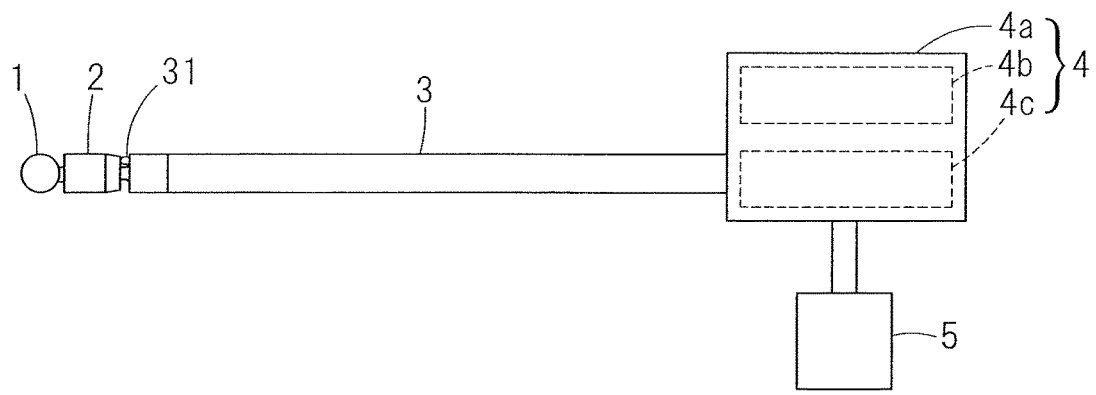
FIG. 1 shows a side view of a schematic configuration of a remote controlled actuator assembly according to the first embodiment of the present invention.
Figure 2:
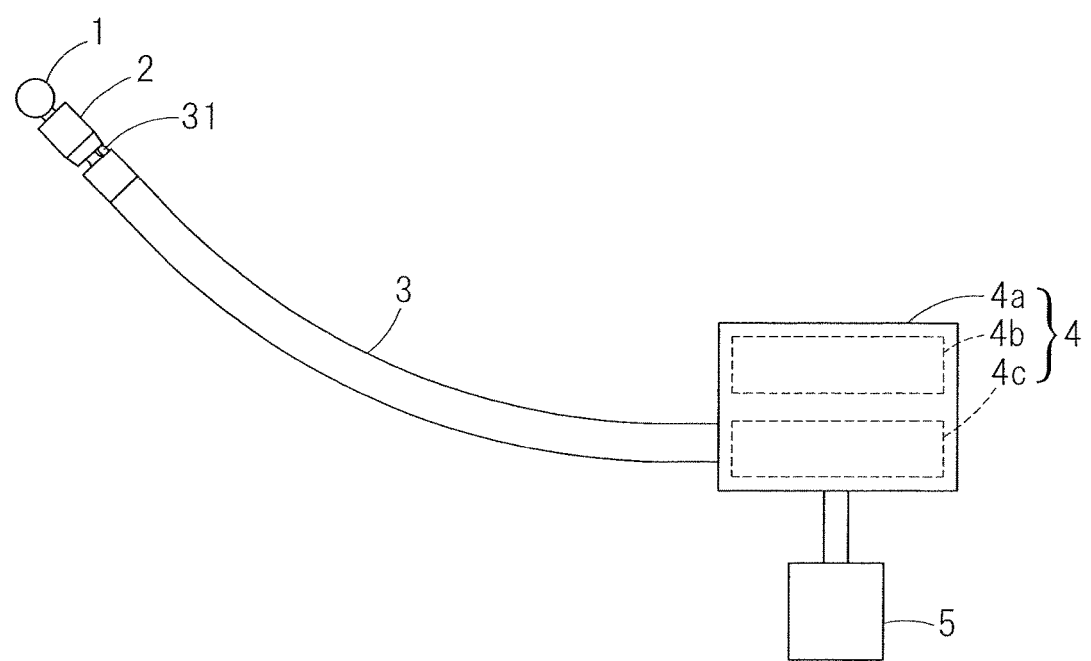
FIG. 2 shows a side view of a spindle guide section according to another example in the first embodiment.

FIG. 1 shows a side view of a schematic configuration of a remote controlled actuator assembly according to the first embodiment of the present invention. FIG. 2 shows a side view of a spindle guide section according to another example in the first embodiment. FIG. 1 and FIG. 2 show similar constructions, except that the spindle guide section 3 as shown in FIG. 1 has a linear shape while the spindle guide section 3 as shown in FIG. 2 includes a curve shape. The schematic configuration of the remote controlled actuator assembly according to the first embodiment will now be described in connection with FIG. 1. This remote controlled actuator assembly includes a distal end member 2 for holding a rotary tool 1, a spindle guide section 3 of an elongated shape having a tip to which the distal end member 2 is fitted for alteration in attitude, a drive unit housing 4a to which a base end of the spindle guide section 3 is connected, and a controller 5 for controlling a tool rotation drive mechanism 4b and an attitude altering drive mechanism 4c, both accommodated within the drive unit housing 4a. The drive unit housing 4a forms a drive unit 4 together with the built-in tool rotation drive mechanism 4b and the similarly built-in attitude altering drive mechanism 4c.

An internal structure of each of the distal end member 2 and the spindle guide section 3 will be described in detail with particular references to FIGS. 3A to 3C. It is to be noted that although FIGS. 3A to 3C illustrate the remote controlled actuator assembly of the type shown in FIG. 1, the respective internal structures of the distal end member 2 and the spindle guide section 3 remain basically the same regardless of whether the spindle guide section 3 is of a linear shape as shown in FIG. 1 or whether the spindle guide section 3 is of a curved shape as shown in FIG. 2.

The distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member connecting unit 15. The distal end member connecting unit 15 supports the distal end member 2 for displacement in attitude and is comprised of a spherical bearing. More specifically, the distal end member connecting unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. In the instance as shown, since the construction is so employed that the distal end member 2 can alter its attitude about an X-axis passing through the center O of curvature, the guide faces F1 and F2 may be cylindrical surface each having its longitudinal axis represented by the X-axis passing through the center O of curvature.

The spindle guide section 3 includes a rotary shaft 22 for transmitting a rotational force exerted by a tool rotating drive source 41 (FIG. 4A) accommodated within the drive unit housing 4a. In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 3C, the spindle 13 and the rotary shaft 22 are coupled together by means of a universal joint 23 for transmitting rotation from the rotary shaft 22 to the spindle 13. The universal joint 23 is made up of a groove 13a, defined in a closed base end of the spindle 13, and of a projection 22a defined in a distal end of the rotary shaft 22 and engageable in the groove 13a. The center of joint between the groove 13a and the projection 22a is located at the same position as the centers of curvature O of the guide faces F1 and F2.

The spindle guide section 3 has an outer shell pipe 25, which forms an outer shell of the spindle guide section 3, and the rotary shaft 22 referred to above is positioned at a center of this outer shell pipe 25. The rotary shaft 22 so positioned is rotatably supported by a plurality of rolling bearings 26 positioned spaced a distant apart from each other in a direction axially of the spindle guide section 3. Between the neighboring rolling bearings 26, spring elements 27A for generating a preload on the inner rings of the corresponding rolling bearing 26 and spring elements 27B for generating the preload on the outer rings of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

Provided between an inner diametric surface of the outer shell pipe 25 and the rotary shaft 22 is a guide pipe 30, having its opposite ends opening. Within a guide hole 30a which is an inner diametric hole of this guide pipe 30, an attitude altering member 31 is reciprocally movably inserted. In the instance as shown, the attitude altering member 31 is in the form of a wire 31a and pillar shaped pins 31b connected to a tip end of the wire 31a. The attitude altering member 31 has a tip end representing a spherical shape which is held in contact with a base end face of the housing 11 of the distal end member 2. The other of the pillar shaped pins 31b that is closer to the drive unit housing 4a also has a tip end representing a spherical shape which is held in contact with a front surface of a linear motion member 51 (FIG. 4A) which will be explained in detail later.

Between a base end face of the housing 11 of the distal end member 2 and a tip end face of the outer shell pipe 25 of the spindle guide section 3, a restoring elastic member 32 made of, for example, a compression coil spring, is arranged at a location spaced 180° degrees circumferentially in phase from the circumferential location where the attitude altering member 31 is positioned. The restoring elastic member 32 biases the distal end member 2 towards a predetermined attitude.

Also, as shown in FIG. 3B, a plurality of reinforcement shafts 34 are arranged, separate from the guide pipe 30, between the inner diametric surface of to the outer shell pipe 25 and the rotary shaft 22 and on the same pitch circle C as that depicted by the guide pipe 30. Those reinforcement shafts 34 are employed for securing the rigidity of the spindle guide section 3. The guide pipe 30 and the plural reinforcement shafts 34 are spaced an equal distance from each other. The guide pipe 30 and the plural reinforcement shafts 34 are held in contact with the inner diametric surface of the outer shell pipe 25 and an outer diametric surface of each of the rolling bearings 26 so as to support the respective outer diametric surfaces of the rolling bearings 26.

Figures 4A, 4B:
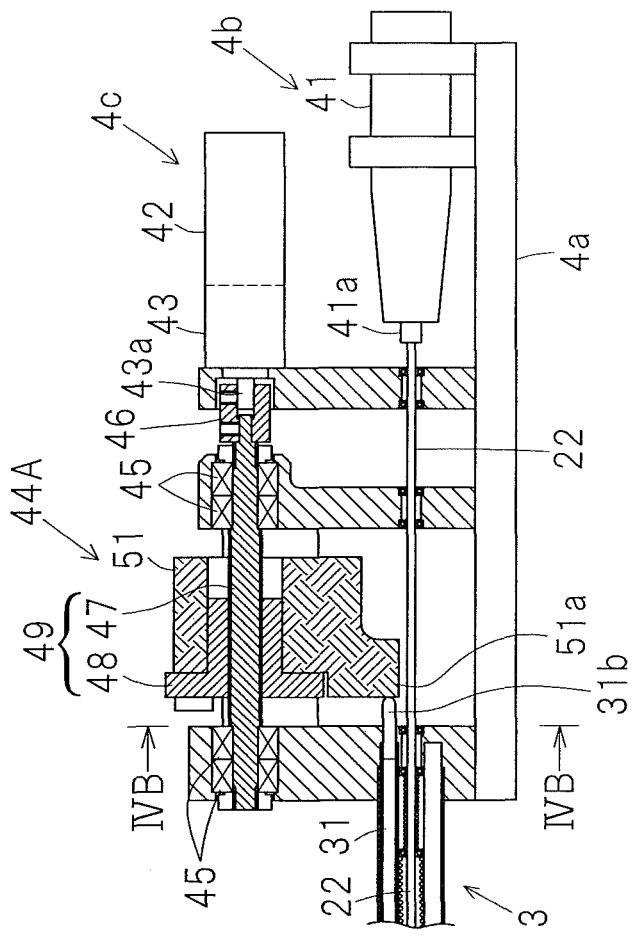
FIG. 4A shows a longitudinal cross sectional view of a tool rotation drive mechanism and an attitude altering drive mechanism of the remote controlled actuator assembly.
FIG. 4B shows a cross sectional view of FIG. 4A taken along the line IVB-IVB, also illustrating a control system.

FIGS. 4A and 4B illustrate the tool rotation drive mechanism 4b and the attitude altering drive mechanism 4c both accommodated within the drive unit housing 4a. The tool rotation drive mechanism 4b includes the tool rotation drive source 41 adapted to be controlled by the controller 5 (best shown in FIGS. 1 and 2). The tool rotation drive source 41 is in the form of, for example, an electrically driven motor having its output shaft 41a coupled with a base end of the rotary shaft 22. The attitude altering drive mechanism 4c includes an attitude altering drive source 42 adapted to be controlled by the controller 5 (best shown in FIGS. 1 and 2). The attitude altering drive source 42 includes a rotary actuator that includes a reduction unit 43 integral with or of one-piece construction with the rotary actuator. The rotary actuator may be an electric actuator or a hydraulic actuator, and in the embodiment under discussion, an electric actuator is used as the rotary actuator. The reduction unit 43 is configured to reduce a speed of rotation from the attitude altering drive source 42 and then to output it. The reduction unit 43 includes an output shaft 43a directly connected to a motion converter mechanism 44A. The motion converter mechanism 44A is configured to convert the rotational output from the reduction unit 43 to advance or retraction motion. The illustrated motion converter mechanism 44A includes a linear motion mechanism configured to convert the rotational output from the reduction unit 43 to a linear back-and-forth motion and then to output it.

In particular, the motion converter mechanism 44A including the linear motion mechanism has a ball screw mechanism 49. The ball screw mechanism 49 includes a ball screw 47 and a nut 48 that is in threaded engagement with the ball screw 47. The ball screw 47 has a first end and a second end opposite to the first end, with the first and second ends being supported by respective bearings 45 and with the first end connecting, via a coupling 46, to the output shaft 43a of the reduction unit 43. The linear motion member 51 described above is fixed to the nut 48, with the linear motion member 51 being guided by a linear guide 50 as shown in FIG. 4B such that the linear motion member 51 is moveable axially of the ball screw 47. The linear motion member 51 forms an output member of the motion converter mechanism 44A. A tip end face of the linear motion member 51 forms a contact portion 51a that contacts a base end of the attitude altering member 31.

Rotation of the output shaft 43a of the reduction unit 43 is converted by the ball screw mechanism 49 to a linear motion that makes the linear motion member 51 move in a linear fashion along the linear guide 50 as shown in FIG. 4B. The movement of the linear motion member 51 to the left side of FIG. 4A pushes the attitude altering member 31, causing the attitude altering member 31 to advance. On the other hand, the movement of the linear motion member 51 to the right side of FIG. 4A causes the attitude altering member 31 to retract, due to the push back caused by the elastic repulsion force of the aforementioned restoring elastic member 32.

As shown in FIG. 4B, the linear motion member 51 is associated with a linear scale 52 whose scale is read by a linear encoder 53 fixed to the drive unit housing 4a. These linear scale 52 and linear encoder 53 form a position detector 54 that is operable to detect an advance or retraction position of the attitude altering member 31. In particular, the output of the linear encoder 53 is transmitted to an advance or retraction position estimator 55 which is configured to estimate an advance or retraction position of the attitude altering member 31. In other words, the position detector 54 is operable to detect an operational position of a power transmission member—formed by the linear motion member 51—which is arranged between the reduction unit 43 and the attitude altering member 31, and the result of the detection is used to estimate an advance or retraction position of the attitude altering member 31.

The advance or retraction position estimator 55 as shown in FIG. 4B includes a relation setting means (not shown), in which the relationship between an advance or retraction position of the attitude altering member 31 and an output signal of the linear encoder 53 is set in terms of an arithmetic equation or table. The advance or retraction position estimator 55 uses the relation setting means to estimate, from a received output signal, an advance or retraction position of the attitude altering member 31. The advance or retraction position estimator 55 may be included in the controller 5 shown in FIG. 1 and FIG. 2, or may be included in an external control device. The controller 5 controls the attitude altering drive source 42 shown in FIG. 4A based on a detection value of the advance or retraction position estimator 55.

An operation of the remote controlled actuator assembly will now be described.

When the tool rotating drive source 41 as shown in FIG. 4A is driven, the rotational force thereof is transmitted to the spindle 13 through the rotary shaft 22 to thereby rotate the tool 1 together with the spindle 13. The tool 1 then being rotated cuts a bone or the like. At this time, the attitude altering drive source 42 is driven and the attitude alteration of the distal end member 2 is performed by remote control. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 3A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 3A. At this time, a pressure from the attitude altering member 31, the elastic repulsive force from the restoring elastic member 32 and a reactive force from the constraint member 21 are applied to the distal end member connecting unit 15 and, depending on the balance of those applied forces, the attitude of the distal end member 2 is determined.

In particular, advance or retraction of the attitude altering member 31 is carried out as described below.

As shown in FIG. 4A, rotation of the attitude altering drive source 42, through the reduction unit 43 that reduces the speed of that rotation, is converted by the motion converter mechanism 44A to advance or retraction motion for transmission to the linear motion member 51 which forms the aforementioned output member. The advance or retraction of the linear motion member 51 is transmitted, via the contact portion 51a, to the pillar shaped pin 31b that is closer to the base end of the attitude altering member 31, thereby causing the attitude altering member 31 to advance or retract. With the provision of the reduction unit 43, even a possibly low output torque from the attitude altering drive source 42 can generate a large torque at an output of the reduction unit 43 thereby to impart a great acting force on the linear motion member 51. This ensures that the advance or retraction of the attitude altering member 31 is carried out, thereby enhancing the positioning accuracy of the tool 1 mounted to the distal end member 2. The provision of the reduction unit 43 leads to reduction in size of the attitude altering drive source 42, thereby making a remote controlled actuator assembly compact as a whole. In particular, as the attitude altering drive source 42 a rotary actuator is used together with a combination of the reduction unit 43 and the motion converter mechanism 44A that converts the rotational output from the reduction unit to advance or retraction motion, and the motion converter mechanism 44A causes via the linear motion member 51 the attitude altering member 31 to advance or retract. For this reason, the reduction in size of the remote controlled actuator assembly as a whole can be realized.

The attitude of the distal end member 2 can be determined based on the advance or retraction position of the attitude altering member 31, which position is detected by the position detector 54 shown in FIG. 4B. The detection value of the position detector 54—more precisely, the detection value of the linear encoder 53—is fed back to the controller 5 for the feedback control of an output value of the attitude altering drive source 42, thereby enhancing the positioning accuracy of the tool 1.

Since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 has a flexible property, the attitude altering operation of the distal end member 2 is carried out accurately even when the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

The remote controlled actuator assembly of the foregoing construction is utilized in grinding the femoral marrow cavity during, for example, the artificial joint replacement surgery and during the surgery, it is used with the distal end member 2 in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely.

There is the necessity that the rotary shaft 22 and the attitude altering member 31 are provided within the spindle guide section 3 of an elongated shape in a protected fashion. Hence, the rotary shaft 22 is provided in the center portion of the outer shell pipe 25 and the guide pipe 30, in which the attitude altering member 31 is accommodated, and the reinforcement shafts 34 are arranged between the outer shell pipe 25 and the rotary shaft 22 so as to be juxtaposed in the circumferential direction. Accordingly, it is possible to protect the rotary shaft 22 and the attitude altering member 31 and, at the same time, the interior can be made hollow to thereby reduce the weight without sacrificing the rigidity. Also, the balance as a whole is good.

Since the outer diametric surfaces of the rolling bearings 26 supporting the rotary shaft 22 are supported by the guide pipes 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

In the embodiment described hereinbefore, as shown in FIG. 4A, the tool rotation drive source 41 and the attitude altering drive source 42 are provided within the common drive unit housing 4a. For this reason, the structure of the remote controlled actuator assembly as a whole can be simplified. It is, however, to be noted that only one of the tool rotation drive source 41 and the attitude altering drive source 42 may be provided within the drive unit housing 4a. Also, as will be explained later, both of the tool rotation drive source 41 and the attitude altering drive source 42 may be provided outside the drive unit housing 4a.

Figure 5A:
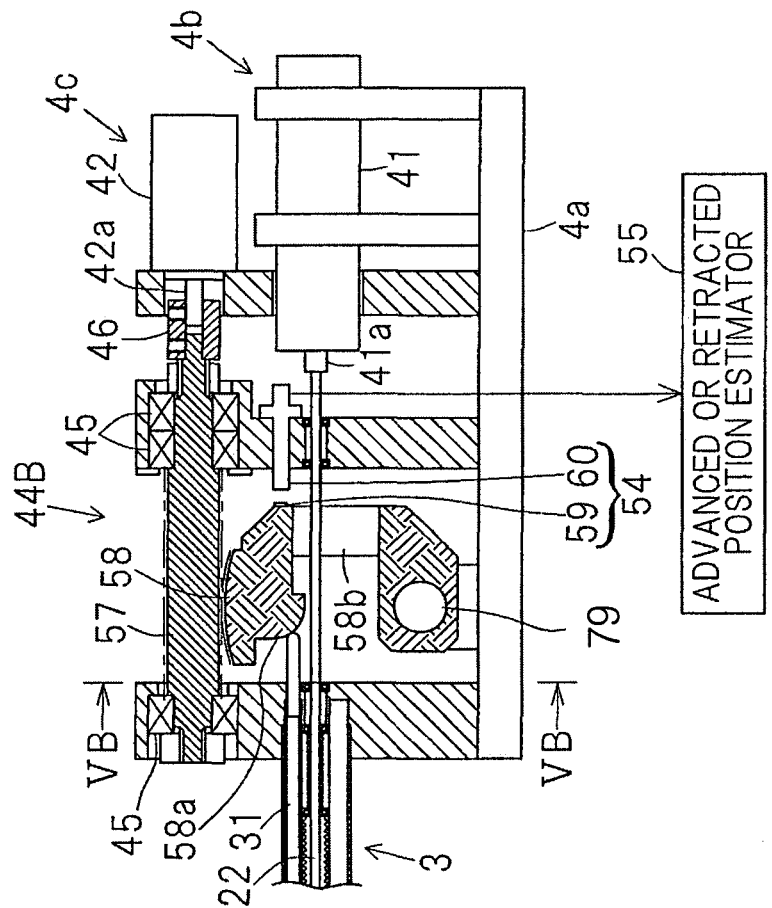
FIG. 5A shows a longitudinal cross sectional view of a tool rotation drive mechanism and an attitude altering drive mechanism of a remote controlled actuator assembly according to the second embodiment of the present invention, also illustrating a control system.
Figure 5B:
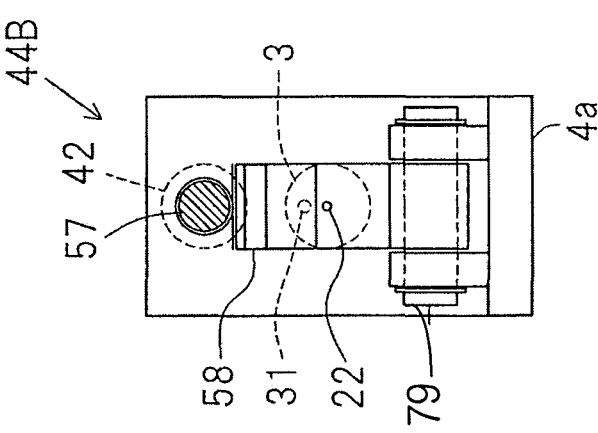
FIG. 5B shows a cross sectional view of FIG. 5A taken along the line VB-VB.
Figure 6A:
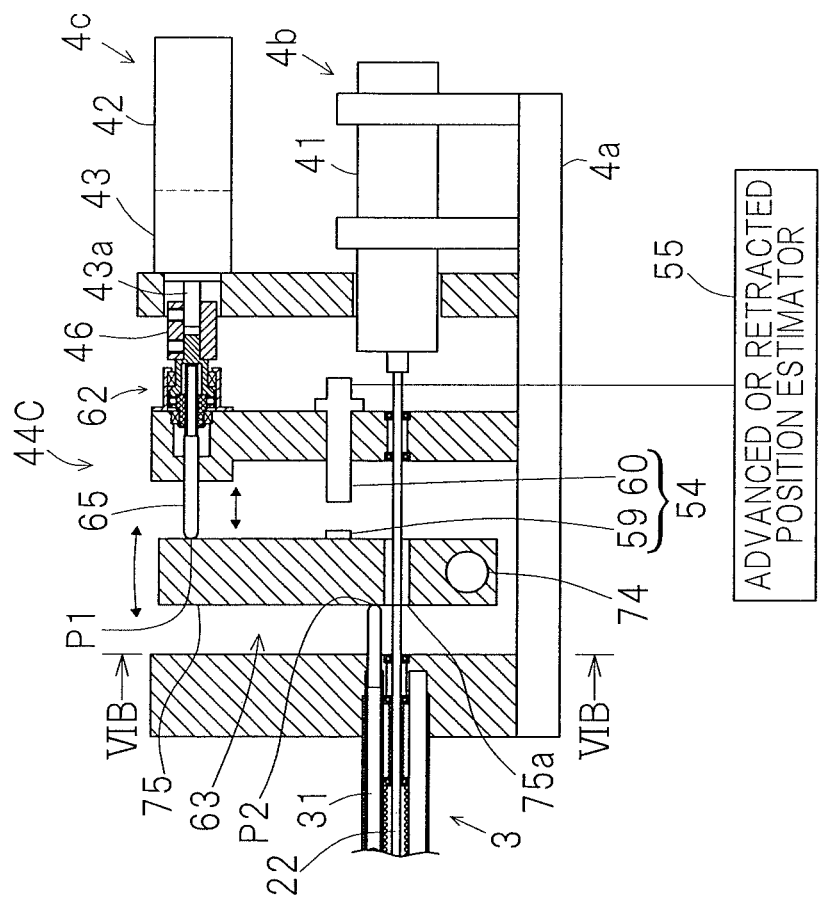
FIG. 6A shows a longitudinal cross sectional view of a tool rotation drive mechanism and an attitude altering drive mechanism of a remote controlled actuator assembly according to the third embodiment of the present invention, also illustrating a control system.
Figure 6B:
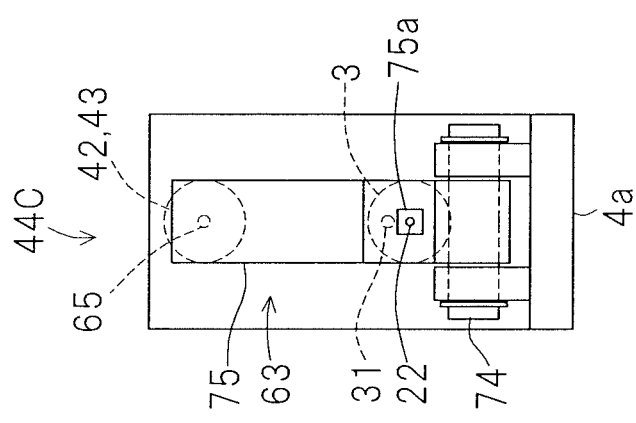
FIG. 6B shows a cross sectional view of FIG. 6A taken along the line VIB-VIB.

FIG. 5A and FIG. 5B illustrate the second embodiment which includes a different motion converter mechanism. The motion converter mechanism 44B not only includes the capability to convert rotation motion to advance or retraction motion but also includes the capability to operate as a reduction device. Hence, the attitude altering drive source 42 is not associated with a reduction unit 43 (FIG. 4A). The motion converter mechanism 44B includes a worm 57 and a worm wheel 58 that is in mesh with the worm 57. The worm 57 has a first end and a second end opposite the first end, with the first and second ends being supported by respective bearings 45 and with the first end connecting, via the coupling 46, to the output shaft 42a of the attitude altering drive source 42. The worm wheel 58 is supported by a support shaft 79. The worm wheel 58 forms an output member of the motion converter mechanism 44B, and the tip end face of the worm wheel 58 forms a contact portion 58a that contacts the base end of the attitude altering member 31. The worm wheel 58 is of a configuration having a circumference, only part of which is provided with teeth, and has an opening 58b to which the rotary shaft 22 is inserted.

Rotation of the output shaft 42a of the attitude altering drive source 42, after the speed thereof has been reduced through a reduction unit including the worm 57 and the worm wheel 58, is transmitted to the worm wheel 58 which operates as the output member. This results in a swing motion of the worm wheel 58 with the contact portion 58a thereof being in a sliding contact with the attitude altering member 31, to cause the attitude altering member 31 to advance or retract. Therefore, pivoting of the contact portion 58a towards the left side of FIG. 5A pushes the attitude altering member 31, causing the attitude altering member 31 to advance. On the other hand, pivoting of the contact portion 58a towards the right side of FIG. 5A results in the push-back of the attitude altering member 31 due to the elastic repulsion force of the restoring elastic member 32, causing the attitude altering member 31 to retract.

An advance or retraction position of the attitude altering member 31 is detected by a position detector 54. In the embodiment under discussion, the position detector 54 includes a detected segment 59 and a detector segment 60 that is configured to detect the displacement of the detected segment 59. The detected segment 59 is associated with a back side (right side of FIG. 5A) of the worm wheel 58, while the detector segment 60 is fixedly provided with the drive unit housing 4a. The position detector 54 may be optical or magnetic. In particular, the output of the detector segment 60 is transmitted to the advance or retraction position estimator 55 which is configured to estimate an advance or retraction position of the attitude altering member 31. In other words, the position detector 54 is operable to detect an operational position of a power transmission member—formed by the worm wheel 58—which is arranged between the reduction unit 43 and the attitude altering member 31, and the advance or retraction position estimator 55 estimates an advance or retraction position of the attitude altering member 31 from the result of the detection.

As mentioned above, the motion converter mechanism 44B includes the capability to operate as a reduction device. In other words, the mechanism including the combination of the worm 57 and the worm wheel 58 is equivalent to a reduction unit equipped with a motion converter capability. This results in a unit integrating a reduction unit and a motion converter mechanism together, thereby reducing the size of the group of components serving as speed reduction and motion conversion functions. Also, the configuration of the worm wheel 58 forming the output member can achieve reduction in the number of components. Furthermore, the reduction unit that includes the worm 57 and the worm wheel 58 can achieve a great reduction ratio.

FIG. 6A, FIG. 6B, FIG. 7A and FIG. 7B illustrate the third embodiment which includes a different motion converter mechanism. The motion converter mechanism 44C includes a linear motion mechanical section 62 configured to convert rotation of the output shaft 43a of the reduction unit 43—which unit 43 is attached to the attitude altering drive source 42—to a linear back-and-forth motion, and a lever mechanical section 63 configured to amplify an output of the linear motion mechanical section 62 and then to transmit such an amplified force to the attitude altering member 31.

Figure 7A:
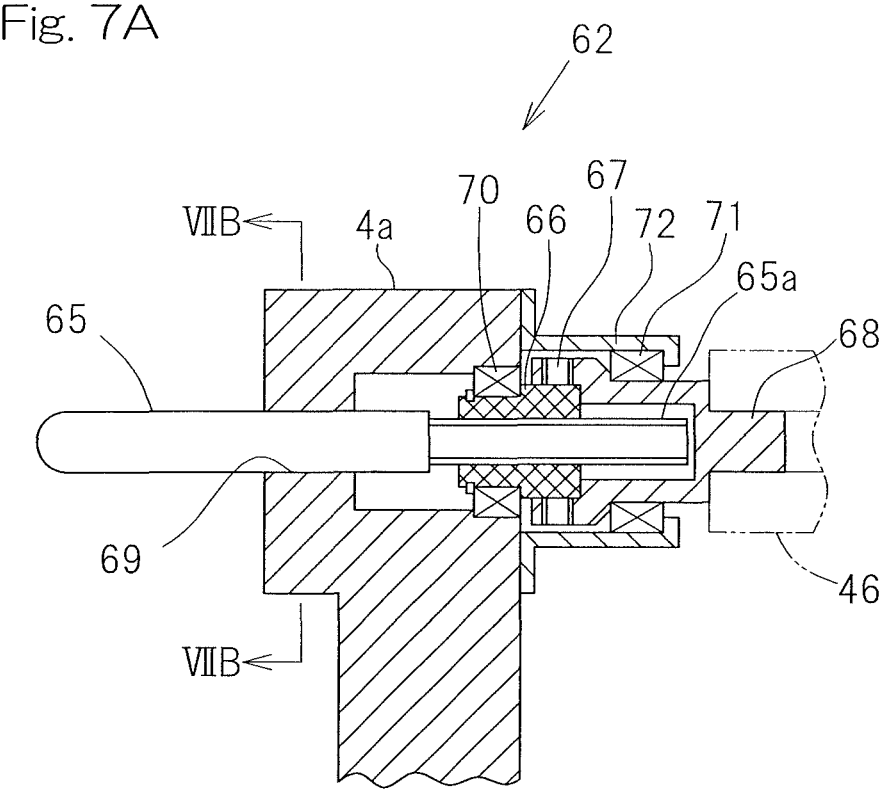
FIG. 7A shows a fragmentary enlarged view of FIG. 6A.
Figure 7B:
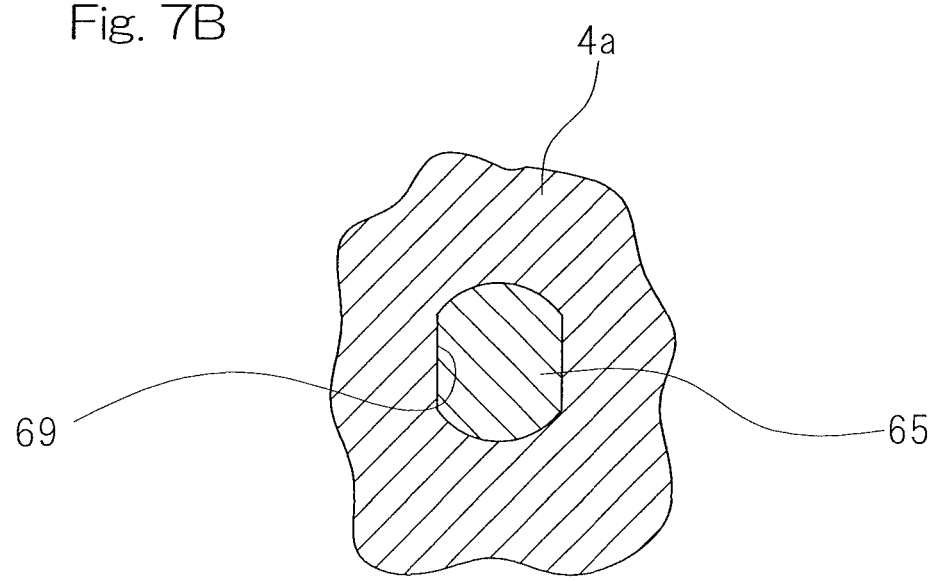
FIG. 7B shows a cross sectional view of FIG. 7A taken along the line VIIB-VIIB.

In other words, the linear motion mechanical section 62 is, as shown on a large scale in FIG. 7A, includes a selective advancing and retracting member 65 provided reciprocally movably in the drive unit housing 4a, a female screw member 66 engaged with a male screw portion 65a of this advancing and retracting member 65, and a connecting member 68 coupled with an outer periphery of the female screw member 66 by means of a connecting pin 67. As shown in FIG. 7B, the advancing and retracting member 65 has a sectional shape, in which opposite side faces thereof are cut out to render them to be flat faces, and, when inserted into a throughhole 69 in the drive unit housing 4a, which is of a sectional shape complemental to the sectional shape of the advancing and retracting member 65, it can be selectively advanced or retracted in a direction conforming to the direction of a center axis, but non-rotatable about the center axis. Referring to FIG. 7A, the female screw member 66 is rotatably supported by the drive unit housing 4a through a bearing 70 and the connecting member 68 is rotatably supported by a support member 72 fixed to the drive housing 4a through a bearing 71. The connecting member 68 is connected with the output shaft 43a of the reduction unit 43 via the coupling 46.

The lever mechanical section 63 includes a pivot lever 75 pivotable about a support pin 74 and is so designed and so configured as to allow a force of the advancing and retracting member 65 to work on a working point P1 of the levers 75, which are respectively spaced a long distance from the support pin 74, and as to apply a force to the attitude altering members 31 at a force point P2, which are spaced a short distance from the support pin 74, wherefore the outputs of the advancing and retracting member 65 can be increased and then transmitted to the attitude altering members 31. The rotary shaft 22 referred to above is made to extend through an opening 75a defined in the pivot lever 75.

An advance or retraction position of the attitude altering member 31 is detected by a position detector 54. In the embodiment under discussion, the position detector 54 includes a detected segment 59 and a detector segment 60 that is configured to detect the displacement of the detected segment 59. The detected segment 59 is associated with a back side of the lever 75, while the detector segment 60 is fixedly provided with the drive unit housing 4a. The position detector 54 may be optical or magnetic. In particular, the output of the detector segment 60 is transmitted to the advance or retraction position estimator 55 which is configured to estimate an advance or retraction position of the attitude altering member 31. In other words, the position detector 54 is operable to detect an operational position of a power transmission member—formed by the lever 75—which is arranged between the reduction unit 43 and the attitude altering member 31, and the advance or retraction position estimator 55 estimate an advance or retraction position of the attitude altering member 31 from the result of the detection.

The configuration of the motion converter mechanism 44C including the linear motion mechanical section 62 converts the rotation of the reduction unit 43 to the linear back-and-forth motion, which, in turn, causes the advance or retraction of the attitude altering member 31. Furthermore, not only does the reduction unit 43 amplify the torque from the attitude altering drive source 42 but also the lever mechanical section 63 amplifies the output of the linear motion mechanical section 62 for output of an amplified force. This results in the advance or retraction motion of the attitude altering member 31 that has a great acting force. The provision of the lever mechanical section 63 allows for use of the reduction unit 43 with a small reduction ratio, thereby achieving reduction in both size and weight of the reduction unit 43. Also, the configuration of the lever mechanical section 63 including the final output stage and the final output stage forming the aforementioned output member can achieve reduction in the number of components.

Figure 8:
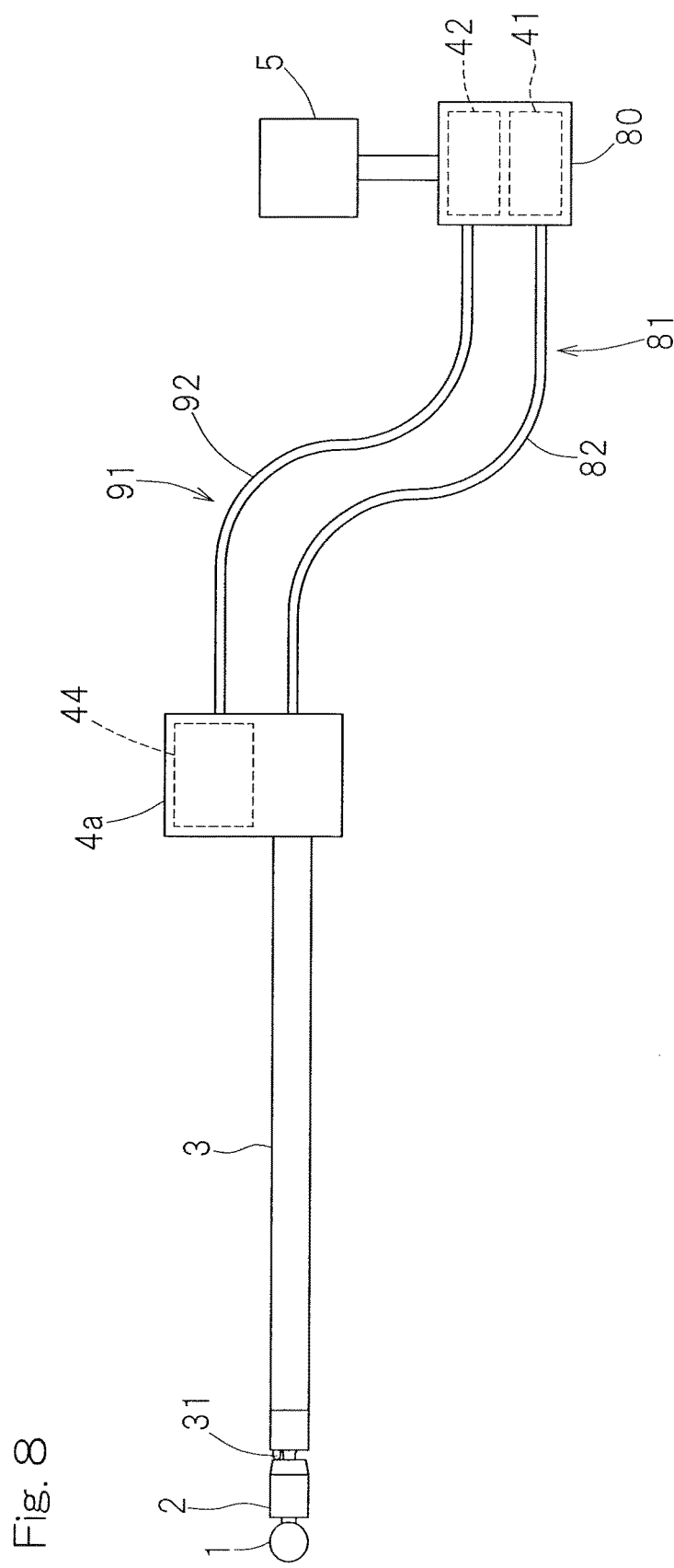
FIG. 8 shows a side view of a schematic configuration of a remote controlled actuator assembly according to the fourth embodiment of the present invention.
Figure 9:
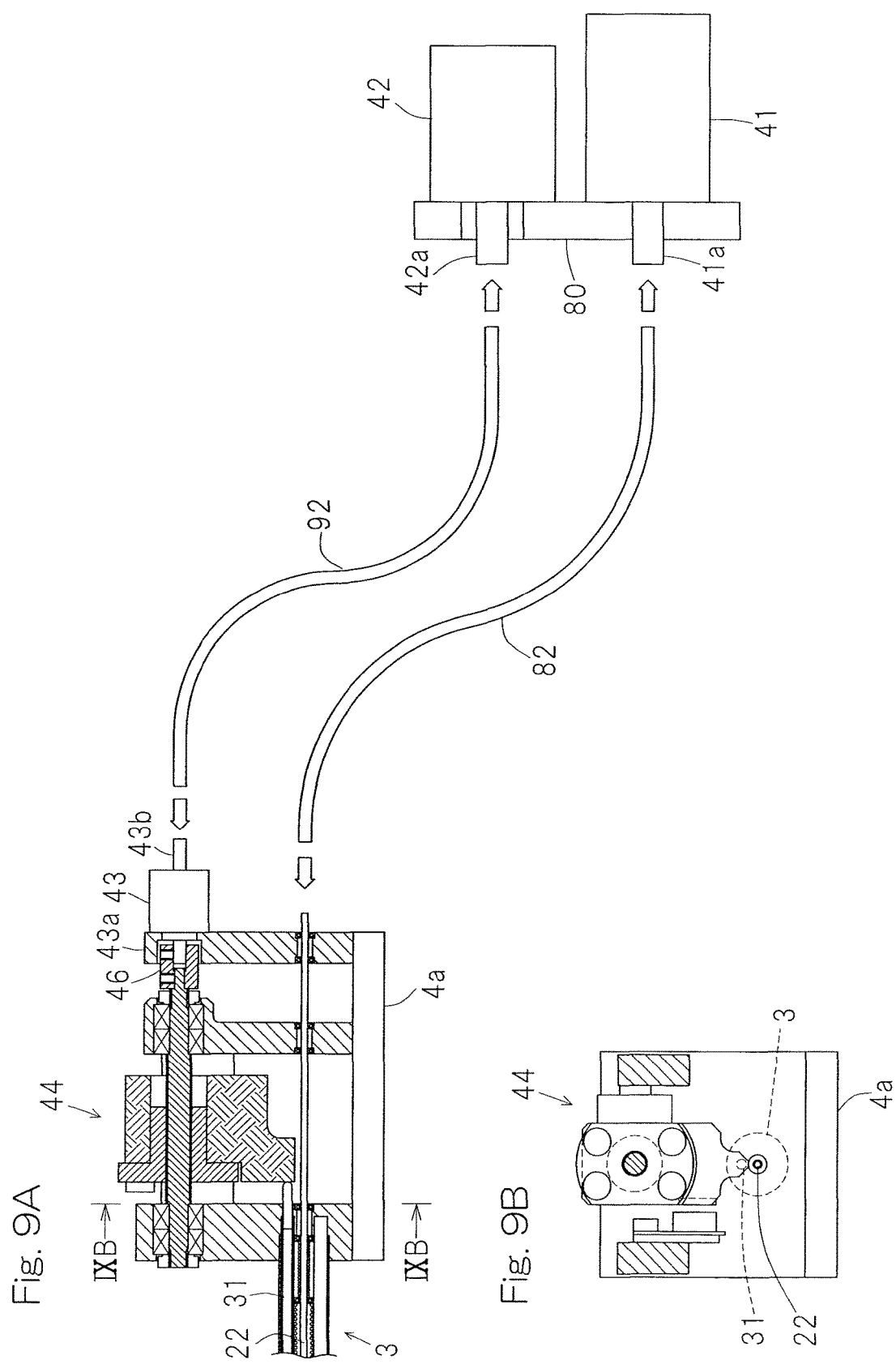
FIG. 9A shows a longitudinal cross sectional view of a tool rotation drive mechanism and an attitude altering drive mechanism of the remote controlled actuator assembly.
FIG. 9B shows a cross sectional view of FIG. 9A taken along the line IXB-IXB.

FIGS. 8, 9A and 9B illustrate a fourth preferred embodiment of the present invention, which make use of the tool rotation drive mechanism of a different structure and the attitude altering drive mechanism of a different structure. While in any one of the previously described embodiments, the tool rotation drive source 41 of the tool rotation drive mechanism 4b and the attitude altering drive source 42 of the attitude altering drive mechanism 4c are provided within the drive unit housing 4a, the fourth embodiment shown in FIGS. 8, 9A and 9B is such that the tool rotation drive source 41 and the attitude altering drive source 42 are provided within a drive source housing 80, which is a member separate from the drive unit housing 4a.

Figure 10:
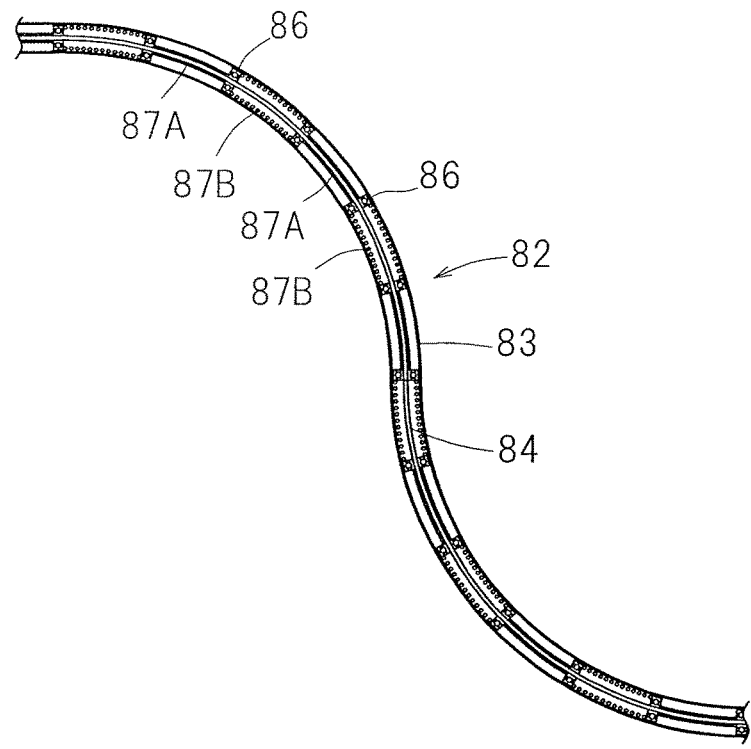
FIG. 10 shows a longitudinal cross sectional view of a tool rotation flexible wire of the tool rotation drive mechanism.

The tool rotation drive mechanism, now identified by 81, that is employed in the practice of this fourth embodiment is operable to transmit the rotation of the output shaft 41a of the tool rotation drive source 41, provided in the drive source housing 80 shown in FIG. 9A, to a base end of the rotary shaft 22 within the drive unit housing 4a by means of an inner wire 84 (shown in FIG. 10) of a tool rotating flexible wire 82. For example, the tool rotating flexible wire 82 may have such a structure as shown in FIG. 10. In other words, at a center of a flexible outer tube 83, the flexible inner wire 84 referred to above is rotatably supported by a plurality of rolling bearings 86. The inner wire 84 has its opposite ends connected respectively with base ends of the output shaft 41a of the tool rotation drive source 41 and the rotary shaft 22. Between the neighboring rolling bearings 86, spring elements 87A and 87B are provided for generating preloads to the rolling bearings 86. Those spring elements 87A and 87B are employed in the form of, for example, compression coil springs. Those spring elements include an inner ring spring element 87A for applying the preload to an inner ring of each of the rolling bearings 86 and an outer ring spring element 87B for applying the preload to an outer ring of each of the rolling bearings 86, and those spring elements 87A and 87B are disposed alternately relative to each other. With the preloads having been applied from the spring elements 87A and 87B to the rolling bearings 86 in this way, the inner wire 84 can be rotated at a high speed. A commercially available flexible shaft may be employed for the tool rotating flexible wire 82.

Figure 11:
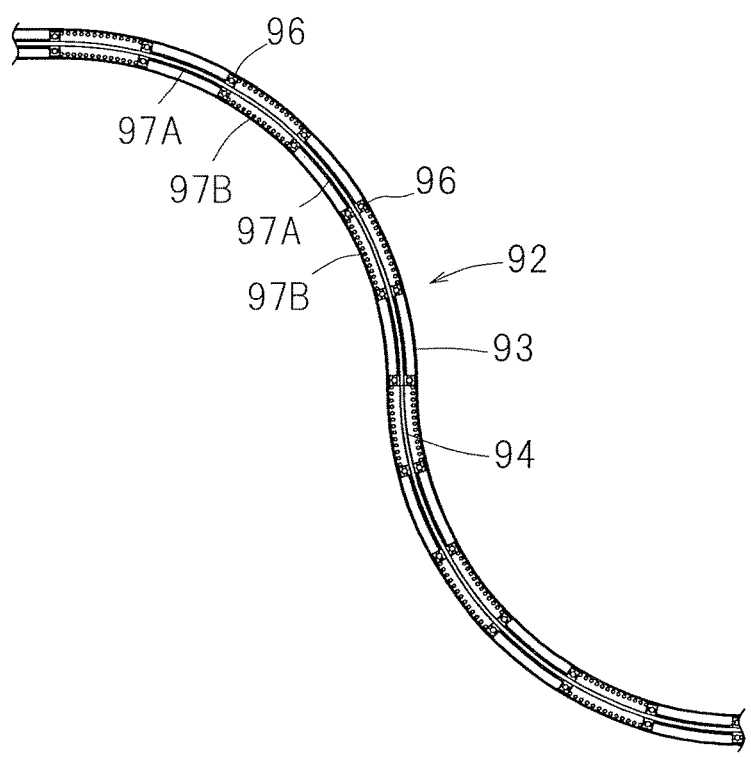
FIG. 11 shows a longitudinal cross sectional view of an attitude altering flexible wire of the attitude altering drive mechanism.

An attitude altering drive mechanism 91 in the embodiment under discussion includes an attitude altering flexible wire 92 that includes an inner wire 94 (FIG. 11). The drive source housing 80 also contains the attitude altering drive source 42. Rotation of the attitude altering drive source 42 is transmitted via the inner wire 94 of the attitude altering flexible wire 92 to the reduction unit 43 in the drive unit housing 4a and then that rotation, a speed of which has been reduced by the reduction unit 43, is transmitted to the motion converter mechanism 44 in the drive unit housing 4a. The motion converter mechanism 44 in the embodiment under discussion has the same configuration as the motion converter mechanism 44A as shown in FIG. 4A and FIG. 4B, thus including a linear motion mechanism configured to convert rotation of the inner wire 94 to a linear back-and-forth motion and then to output it. In the figures, some of the elements or features having the same construction/configuration as those shown in FIG. 4A and FIG. 4B are provided with like numerals. As the motion converter mechanism 44, other type of a motion converter mechanism, i.e. the aforementioned motion converter mechanism 44B, 44C or another motion converter mechanism 44D which will be described later, may be employed.

The attitude altering flexible wire 92 is of the same structure as the tool rotating flexible wire 82 and takes such a structure as shown in FIG. 11. In other words, at a center of a flexible outer tube 93, the flexible inner wire 94 is rotatably supported by a plurality of rolling bearings 96. The inner wire 94 has its opposite ends connected respectively with the output shaft 42a of the attitude altering drive source 42 and the input shaft 43b of the reduction unit 43. Between the neighboring rolling bearings 96, spring elements 97A and 97B are provided for generating preloads to the rolling bearings 96. Those spring elements 97A and 97B are employed in the form of, for example, compression coil springs. There are an inner ring spring element 97A for applying the preload to an inner ring of each of the rolling bearings 96 and an outer ring spring element 97B for applying the preload to an outer ring of each of the rolling bearings 96, and those spring elements 97A and 97B are disposed alternately relative to each other. With the preloads having been applied from the spring elements 97A and 97B to the rolling bearings 96 in this way, the inner wire 94 can be rotated at a high speed. A commercially available flexible shaft may be employed for the attitude altering flexible wire 92.

The inner wire 94 of the attitude altering flexible wire 92 may be twisted while transmitting rotation, resulting in rotational phase offset between the upstream part and the downstream part of the inner wire 94 with respect to the path of transmission of rotation. Nevertheless, the configuration of the reduction unit 43 being downstream of the flexible wire 92 in the path of transmission of rotation can reduce the rotational phase offset on the output side of the reduction unit 43. Hence, the twisting of the flexible wire 92 does not affect the output member—formed by the linear motion member 51—thereby allowing for precise advance or retraction of the attitude altering member 31.

Figure 12:
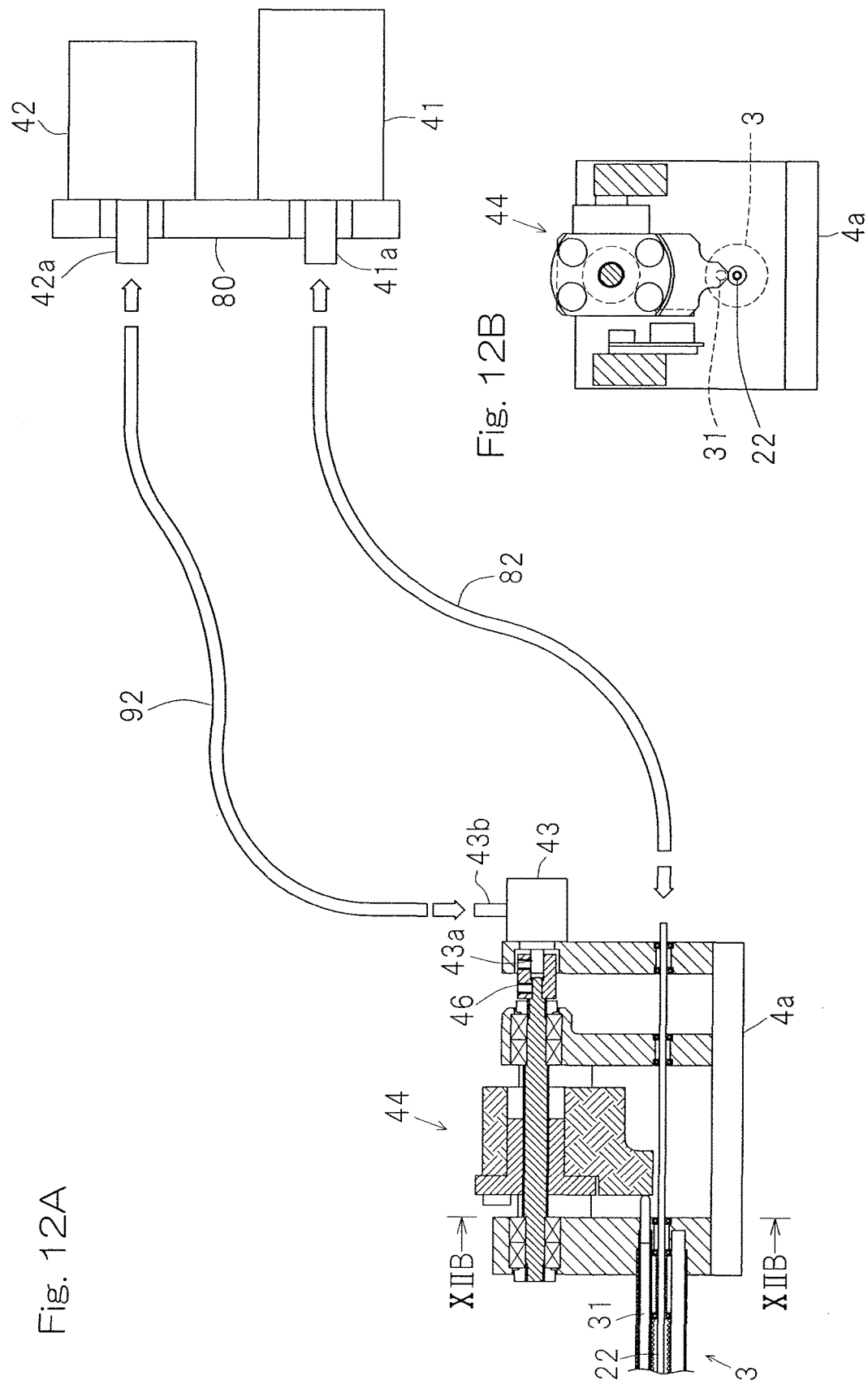
FIG. 12A shows a longitudinal cross sectional view of a variant of the fourth embodiment.
FIG. 12B shows a cross sectional view of FIG. 12A taken along the line XIIB-XIIB.

In the fourth embodiment as shown in FIG. 8, FIG. 9A and FIG. 9B, the input 43b and the output shaft 43a of the reduction unit 43 are aligned with a common axis. As shown in FIG. 12A and FIG. 12B that illustrates a variant of the fourth embodiment, the input shaft 43b and the output shaft 43a may be perpendicular to each other. For the reduction unit 43 such as the one according to the fourth embodiment that includes input and output shafts 43b, 43a that are aligned with a common axis, a harmonic drive unit or a planetary gear unit may be employed. These units can achieve a great reduction ratio, in spite of their compact constructions. In the case of the reduction unit 43 such as the one according to a variant of the fourth embodiment that includes input and output shafts 43b, 43a that are perpendicular to each other, design freedom can be enhanced, since the attitude altering drive source 42 does not have to be located on an extension line of the output shaft 43a of the reduction unit 43.

Figure 13:
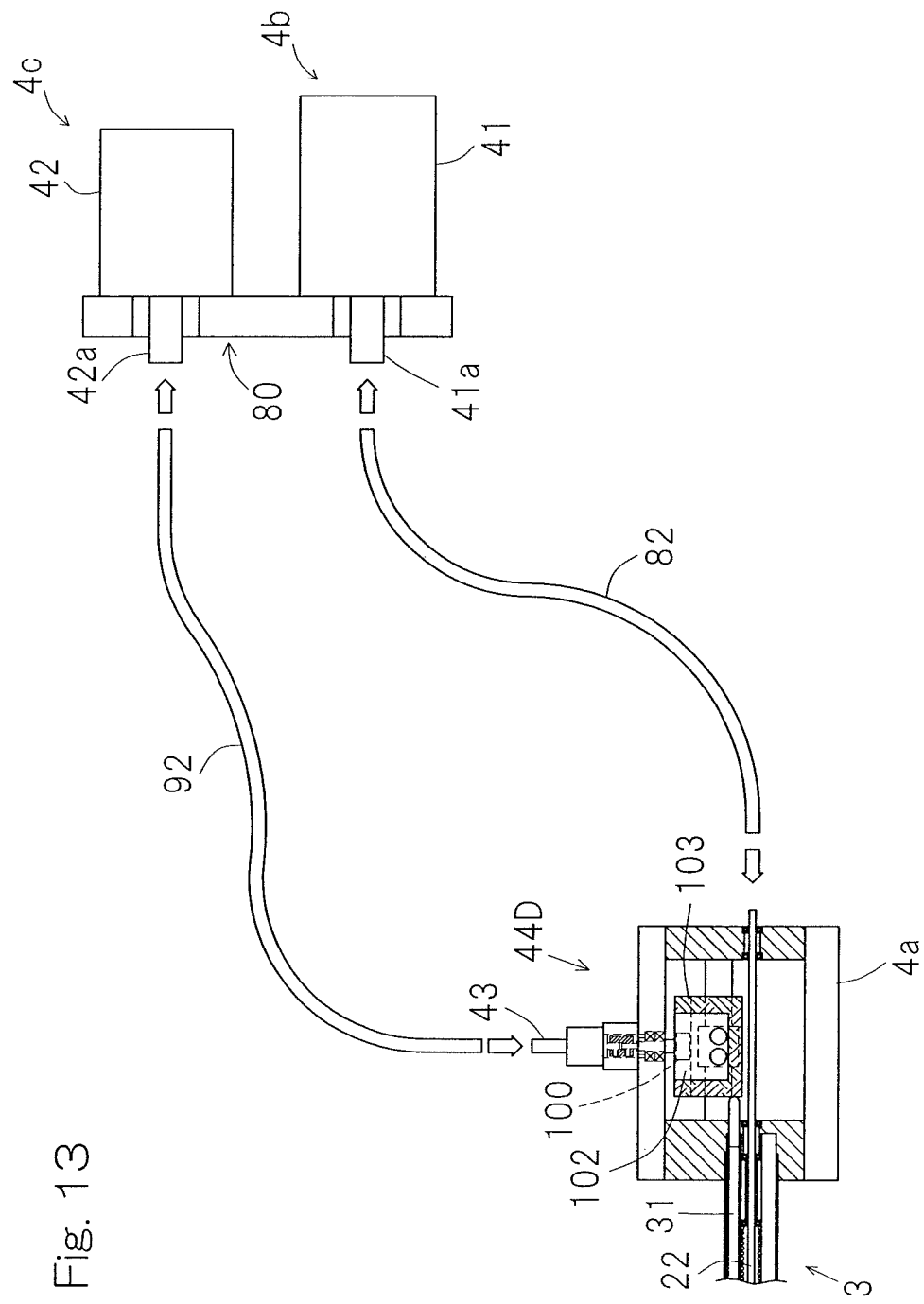
FIG. 13 shows a longitudinal cross sectional view of a tool rotation drive mechanism and an attitude altering drive mechanism of a remote controlled actuator assembly according to the fifth embodiment of the present invention.
Figure 14A:
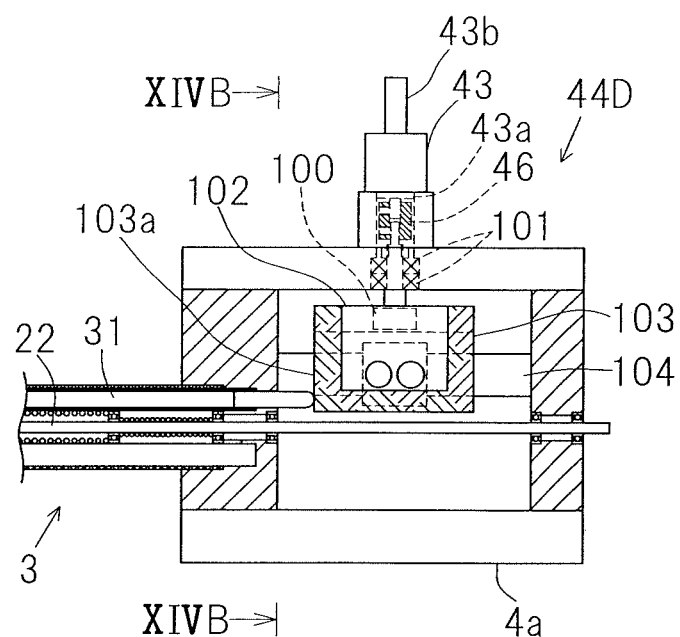
FIG. 14A shows a fragmentary enlarged view of FIG. 13.
Figure 14B:
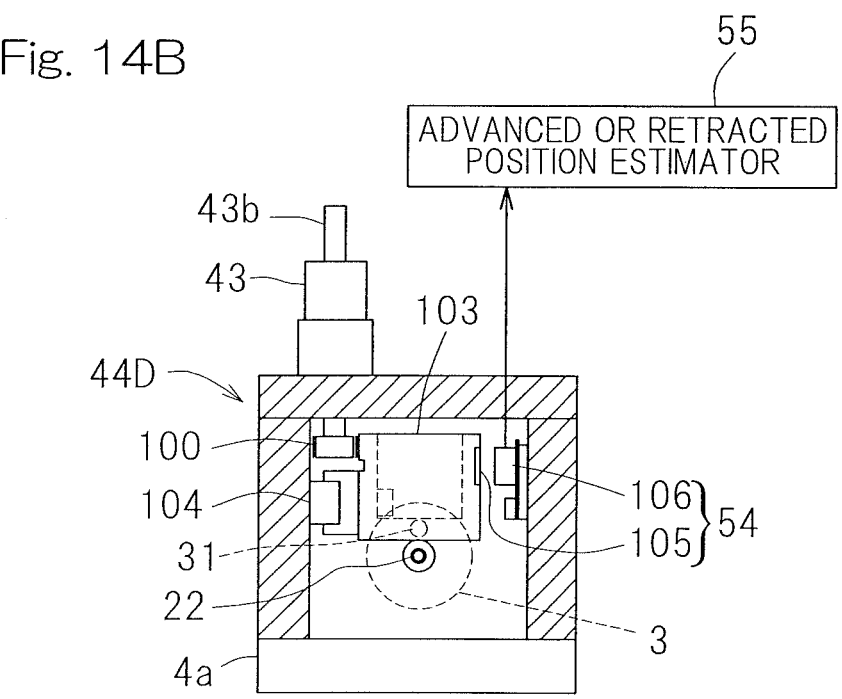
FIG. 14B shows a cross sectional view of FIG. 14A taken along the line XIVB-XIVB, also illustrating a control system.

FIG. 13, FIG. 14A and FIG. 14B illustrate the fifth embodiment, in which the tool rotation drive source 41 of the tool rotation drive mechanism 4b and the attitude altering drive source 42 of the attitude altering drive mechanism 4c are in the drive source housing 80 that is separate from the drive unit housing 4a, with the configuration of the motion converter mechanism being different from the previous embodiments. The motion converter mechanism 44D includes a linear motion mechanism employing a rack and a pinion, and, in particular, includes a pinion 100 that connects via a coupling 46 to the output shaft 43a of the reduction unit 43 in the drive unit housing 4a. The pinion 100 is rotatably supported via a bearing 101. The pinion 100 is in mesh with a rack 102. The rack 102 is formed integrally with an output member 103 or formed as one-piece construction with the output member 103. The output member 103 is supported by a linear guide 104 such that the output member 103 is moveable in a longitudinal direction of the attitude altering member 31. The output member 103 has a tip end face that forms a contact portion 103a to contact the base end of the attitude altering member 31.

Rotation of the output shaft 43a of the reduction unit 43 is converted by the rack 102 and the pinion 100 to a linear back-and-forth motion that is transmitted to the output member 103. The movement of the output member 103 to the left side of FIG. 14A pushes the attitude altering member 31, causing the attitude altering member 31 to advance. On the other hand, the movement of the output member 103 to the right side of FIG. 14A causes the attitude altering member 31 to retract, due to the push back caused by the elastic repulsion force of the aforementioned restoring elastic member 32.

As shown in FIG. 14B, the output member 103 is associated with a linear scale 105 whose scale is read by a linear encoder 106 fixed to the drive unit housing 4a. These linear scale 105 and linear encoder 106 form a position detector 54 that is operable to detect an advance or retraction position of the attitude altering member 31. Similarly to the previously mentioned embodiment(s), the output of the linear encoder 106 is transmitted to the advance or retraction position estimator 55 which is configured to estimate the advance or retraction position of the attitude altering member 31. In other words, the position detector 54 is operable to detect an operational position of a power transmission member—formed by the output member 103—which is arranged between the reduction unit 43 and the attitude altering member 31, and the advance or retraction position estimator 55 estimates an advance or retraction position of the attitude altering member 31 from the result of the detection.

The configuration of the motion converter mechanism 44D including the rack 102 and the pinion 100 may be applied to the remote controlled actuator assembly with the drive unit housing 4a containing the attitude altering drive source 42. Although FIG. 14A illustrates the reduction unit 43 including the input shaft 43b and the output shaft 43a that are aligned with a common axis, the input shaft 43b and the output shaft 43a of the reduction unit 43 may be perpendicular to each other.

FIGS. 15A and 15B illustrate a first variant of the fifth preferred embodiment of the present invention, in which a different structure is employed for altering the attitude of the distal end member 2. This remote controlled actuator assembly includes two guide pipes 30 spaced 180 degrees in phase relative to each other within an outer shell pipe 25 and each of the guide pipes 30 has an inner diametric hole functioning as a guide hole 30a within which an attitude altering member 31 comprised of the wire 31a and the pillar shaped pins 31b in a manner similar to those described hereinbefore is inserted for advancement and retraction. Between those two guide pipes 30, a plurality of reinforcement shafts 34 are arranged on the same pitch circle diameter C as that of the guide pipes 30. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown) is provided with two attitude altering drive sources 42 (not shown) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 15A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 15A. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 15A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by a single attitude altering member 31, the attitude stability of the distal end member 2 can be increased.

Figure 16A:
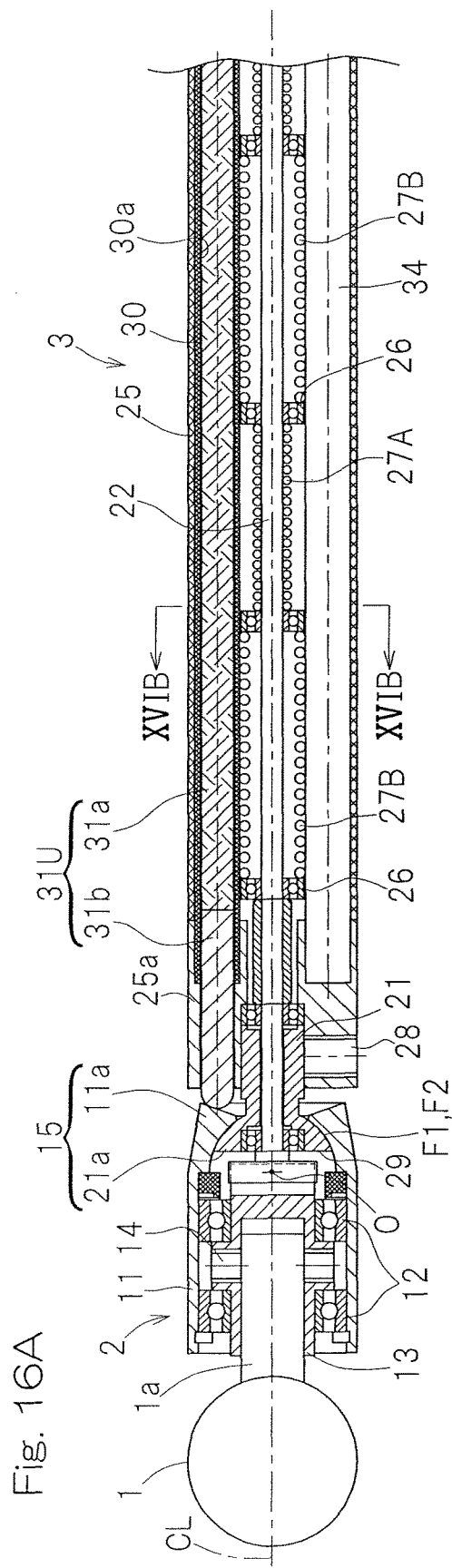
FIG. 16A shows a longitudinal cross sectional view of a distal end member and a spindle guide section of a remote controlled actuator assembly according to the second variant which also differs in the system for altering the distal end member.
Figure 16B:
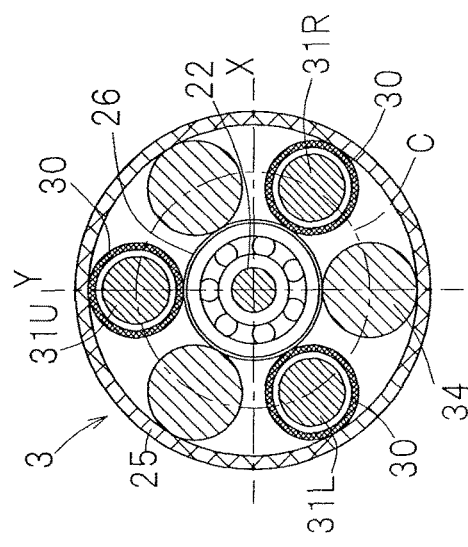
FIG. 16B shows a cross sectional view of FIG. 16A taken along the line XVIB-XVIB.

FIGS. 16A and 16B illustrate a second variant of the fifth preferred embodiment, in which the structure for altering the attitude of the distal end member 2 is further different. In this remote controlled actuator assembly, three guide pipes 30 are employed and arranged at respective circumferential locations spaced 120° in phase from each other within the outer shell pipe 25, and the attitude altering member 31 is reciprocally movably inserted in each of the guide holes 30a, which are inner diametric holes of such guide holes 30a, in a manner similar to that described hereinbefore. Among the three guide pipes 30, a plurality of reinforcement shafts 34 are arranged on the same pitch circle C as that of the guide pipes 30. No resilient restoring member 32 is employed. The guide faces F1 and F2 represent spherical faces having a center of curvature at a point O and the distal end member 2 can be tilted in any arbitrarily chosen direction.

The drive unit 4 is provided with three attitude altering drive sources 42 (42U, 42L and 42R), best shown in FIGS. 18A, 18B, 19A and 19B, for selectively advancing or retracting respective attitude altering members 31 (31U, 31L and 31R) and, accordingly, the attitude of the distal end member 2 is altered by driving those three attitude altering drive sources 42 in liaison with each other.

By way of example, when one of the attitude altering members 31U, upper side one as viewed in FIG. 16B, is advanced towards the distal, tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the distal, tip end side consequently oriented downwardly as viewed in FIG. 16A. At this time, those attitude altering drive sources 42 are controlled so that the amount of advance or retraction of each of the attitude altering members 31 may become proper. On the other hand, when each of those attitude altering members 31 is retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 16A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 16A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. If the number of the attitude altering members 31 is increased, the attitude stability of the distal end member 2 can be yet further increased.

Figure 17A:
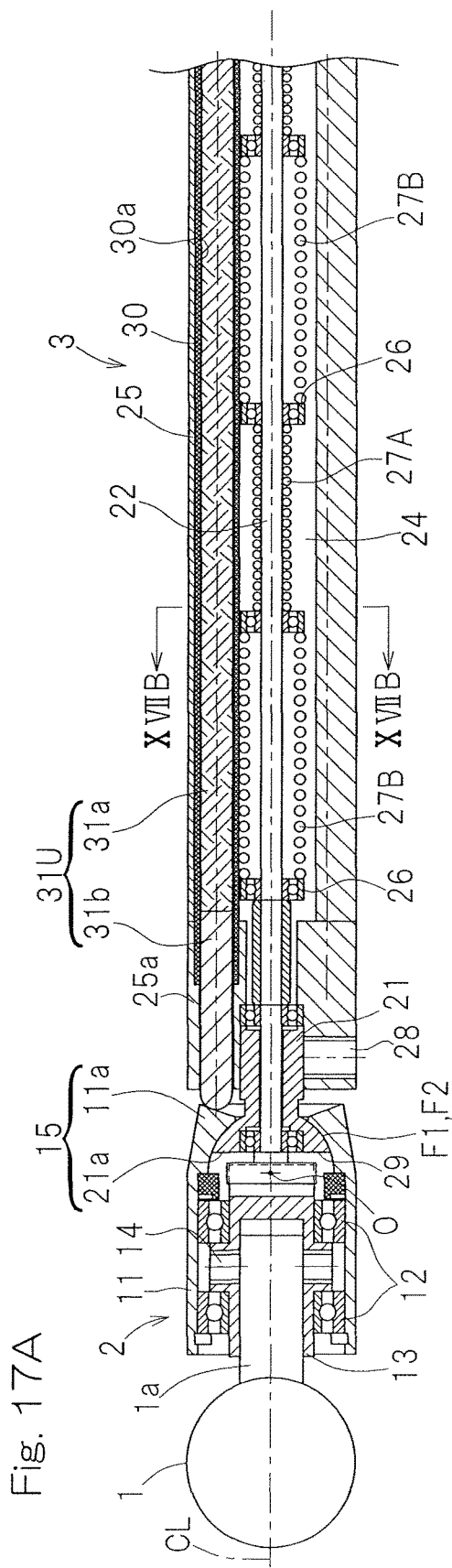
FIG. 17A shows a longitudinal cross sectional view of a distal end member and a spindle guide section of a remote controlled actuator assembly according to the third variant which also differs in the system for altering the distal end member.
Figure 17B:
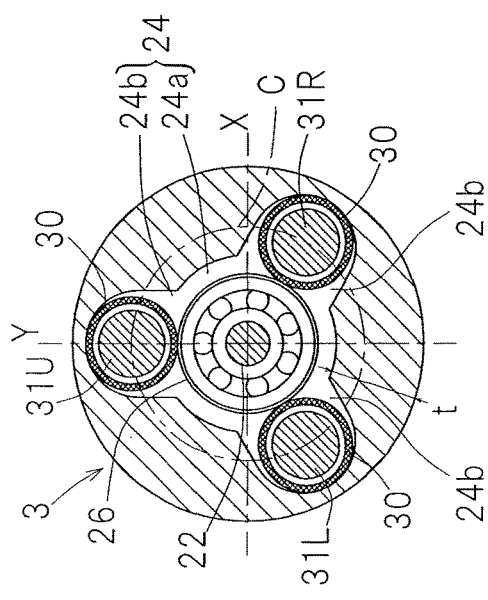
FIG. 17B shows a cross sectional view of FIG. 17A taken along the line XVIIB-XVIIB.

FIGS. 17A and 17B illustrate a third variant of the fifth preferred embodiment, in which the spindle guide section 3 has an internal structure different from the second variant shown in and described with reference to FIGS. 16A and 16B. The spindle guide section 3 employed in this remote controlled actuator assembly is such that the outer shell pipe 25 has a hollow hole 24 made up of a round hole portion 24a at a center thereof and three grooved portions 24b formed on an outer periphery of the round hole portion 24a so as to be depressed radially outwardly from respective circumferential positions spaced 120° from each other. Each of the grooved portions 24b has a tip, a peripheral wall of which represents a semicircular shape in section. The rotary shaft 22 and the rolling bearings 26 are accommodated within the round hole portion 24a, and the attitude altering member 31 (31U, 31L and 31R) is accommodated within each of grooved portions 24b.

Figure 18A:
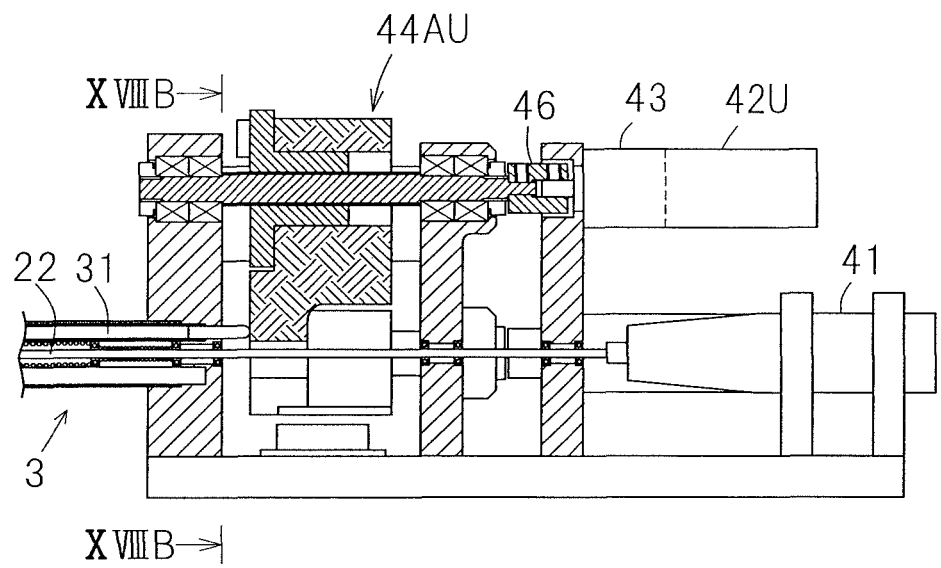
FIG. 18A shows a longitudinal cross sectional view of the configuration of a tool rotation drive mechanism and an attitude altering drive mechanism of the remote controlled actuator assembly as shown in FIG. 16A and FIG. 16B.
Figure 18B:
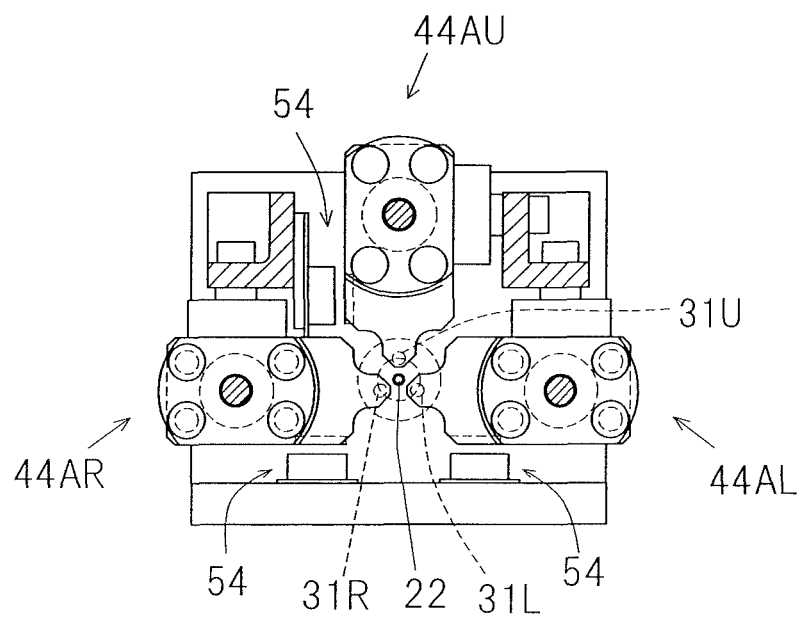
FIG. 18B shows a cross sectional view of FIG. 18A taken along the line XVIIIB-XVIIIB.
Figure 19A:
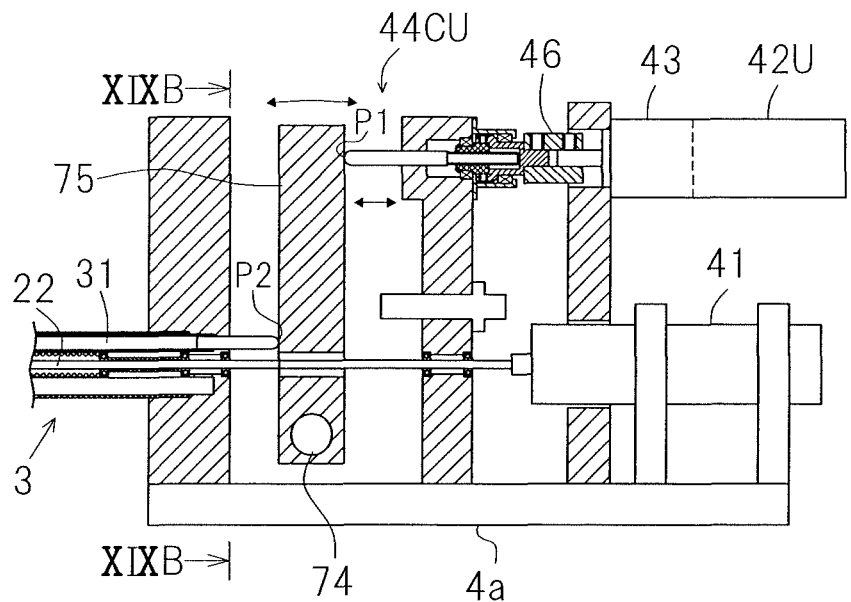
FIG. 19A shows a longitudinal cross sectional view of another exemplary configuration of the tool rotation drive mechanism and the attitude altering drive mechanism.
Figure 19B:
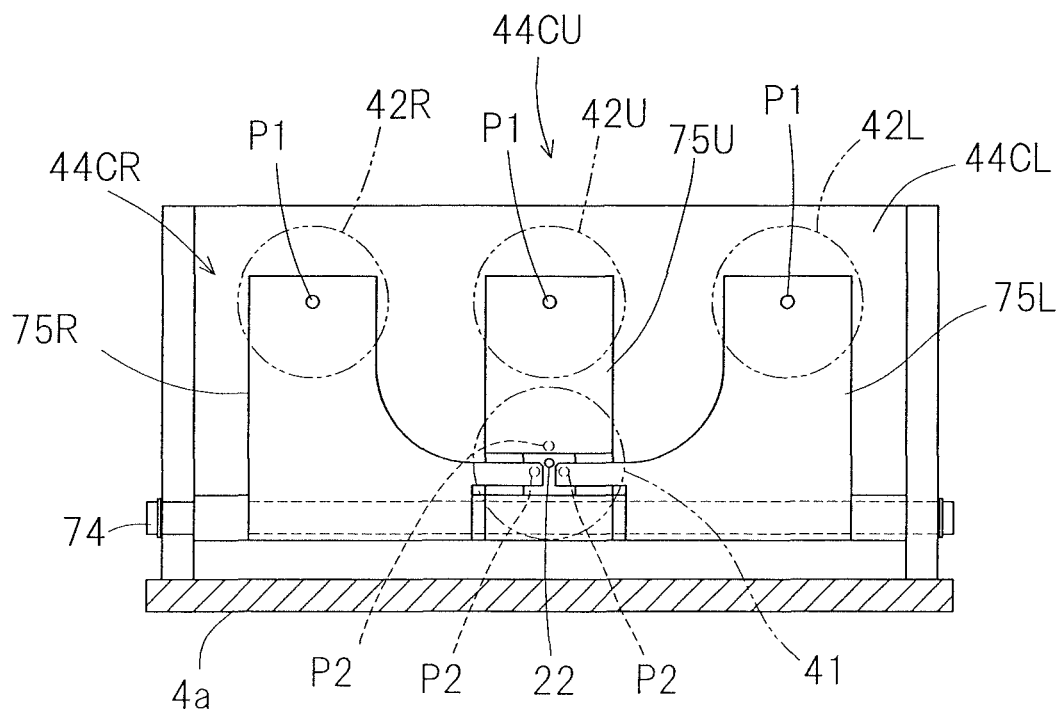
FIG. 19B shows a cross sectional view of FIG. 19A taken along the line XIXB-XIXB.

Since the outer shell pipe 25 is made to have the above described sectional shape, the wall thickness t of portions of the outer shell pipe 25 other than the grooved portions 24b increases and as a result, the geometrical moment of inertia of the outer shell pipe 25 becomes large. In other words, the rigidity of the spindle guide section 3 is increased. Accordingly, not only can the positioning accuracy of the distal end member 2 be increased, but the cutting capability can also be increased. Also, since the guide pipes 30 are arranged within the grooved portions 24b, the positioning of the guide pipes 30 in the circumferential direction can be facilitated and as a result, the assemblability is good.

Where the attitude altering members 31 are provided at three circumferential locations such as in the second variant shown in FIG. 16A and FIG. 16B or in the third variant shown in FIG. 17A and FIG. 17B, the attitude altering drive mechanism 4c may be designed to have such a configuration as shown in FIG. 18A and FIG. 18B or in FIG. 19A and FIG. 19B. In particular, may be provided three attitude altering drive sources 42 (42U, 42L, 42R) that are operable to cause three, respective attitude altering members 31 (31U, 31L, 31R) to advance or retract independently of each other, along with three motion converter mechanisms 44AU, 44AL, 44AR (FIG. 18B) or three motion converter mechanisms 44CU, 44CL, 44CR (FIG. 19B) associated with the respective attitude altering drive sources 42. Each of the motion converter mechanisms 44AU, 44AL, 44AR as shown in FIG. 18A and FIG. 18B has the same configuration as that of the motion converter mechanism 44A of a linear motion mechanism type shown in FIG. 4A and FIG. 4B. The motion converter mechanisms 44AU, 44AL, 44AR are disposed in a radial fashion around a rotary shaft 22. Each of the motion converter mechanisms 44CU, 44CL, 44CR as shown in FIG. 19A and FIG. 19B has the same configuration as that of the motion converter mechanism 44C, which includes the linear motion mechanical section 62 and the lever mechanical section 63, shown in FIG. 6A, FIG. 6B, FIG. 7A and FIG. 7B. The motion converter mechanisms 44CU, 44CL, 44CR are disposed in a juxtaposed fashion laterally from right to left.

Although the spindle guide section 3 employed in the practice of any one of the foregoing embodiments has been shown and described as having a linear shape, the remote controlled actuator assembly of the present invention is effective in that even when the attitude altering member 31 is flexible and the spindle guide section 3 has a curved portion, the attitude alteration operation of the distal end member 2 is assuredly effected and, therefore, a portion of or the whole of the spindle guide section 3 may be so formed as to have a curved shape as shown in FIG. 2. If the spindle guide section 3 is of a curved configuration, it may occur that the distal end member 2 can be inserted deep into the bone where it fails to reach if having a linear shape, and the processing of the artificial joint insertion hole during the artificial joint replacement surgery can be precisely finished.

Where the spindle guide section 3 is so formed as to have the curved shape, the outer shell pipe 25, the guide pipe 30 and the reinforcement shaft 34 have to be curved in shape correspondingly. Also, the use of an easily deformable material for the rotary shaft 22 is preferred and, for example, a shape memory alloy can be suitably employed therefor.

Although the present invention has been fully described in connection with the embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE SIGNS

1: TOOL
2: DISTAL END MEMBER
3: SPINDLE GUIDE SECTION
4a: DRIVE UNIT HOUSING
5: CONTROLLER
13: SPINDLE
15: DISTAL END MEMBER CONNECTING UNIT
22: ROTARY SHAFT
30: GUIDE PIPE
30a: GUIDE HOLE
31: ATTITUDE ALTERING MEMBER
41: TOOL ROTATION DRIVE SOURCE
42: ATTITUDE ALTERING DRIVE SOURCE
43: REDUCTION UNIT
43a: OUTPUT SHAFT
43b: INPUT SHAFT
44, 44A, 44B, 44C, 44D: MOTION CONVERTER MECHANISM
49: BALL SCREW MECHANISM
51: LINEAR MOTION MEMBER (OUTPUT MEMBER)
51a: CONTACT PORTION
54: POSITION DETECTOR
57: WORM
58: WORM WHEEL (OUTPUT MEMBER)
58a: CONTACT PORTION
62: LINEAR MOTION MECHANICAL SECTION
63: LEVER MECHANICAL SECTION
75: LEVER (OUTPUT MEMBER)
75a: OPENING
92: ATTITUDE ALTERING FLEXIBLE WIRE
100: PINION
102: RACK
103: OUTPUT MEMBER

What is claimed is:

1. A remote controlled actuator assembly comprising:
a spindle guide section having an elongated shape;
a distal end member fitted to a tip end of the spindle guide section through a distal end member connecting unit for alteration in attitude;
a tool rotatably provided in the distal end member;
a tool rotation drive source for rotating the tool; and
an attitude altering drive mechanism for operating the attitude of the distal end member,
wherein the distal end member rotatably supports a spindle for holding the tool,
wherein an interior of the spindle guide section accommodates a rotary shaft for transmitting a rotation of the tool rotation drive source to the spindle and a guide hole having its opposite ends open,
wherein a flexible attitude altering member is positioned reciprocally movable within the guide hole, and has a tip of the attitude altering member for undergoing a reciprocating or retracting motion in contact with the distal end member so as to alter the attitude of the distal end member about an axis perpendicular to a longitudinal axis of the spindle, and
wherein the attitude altering drive mechanism includes
an attitude altering drive source including a rotary actuator, and
a motion converter mechanism configured to convert a rotational output from the attitude altering drive source to an advancing or retracting motion, the motion converter mechanism comprising a worm that is rotated by rotation of the attitude altering drive source and a worm wheel that is in mesh with the worm, the worm wheel forming an output member having a contact portion that slidingly contacts a base end of the attitude altering member and is operable to cause the attitude altering member to advance or retract,
wherein the worm wheel has a circumference, only part of which is provided with teeth, and has an opening to which the rotary shaft is inserted.

2. The remote controlled actuator assembly as claimed in claim 1, wherein the motion converter mechanism includes a linear motion mechanism configured to convert a rotational output from the attitude altering drive source to a linear back-and-forth motion, and the linear motion mechanism includes a final output stage forming the output member.

3. The remote controlled actuator assembly as claimed in claim 1, further comprising a position detector operable to detect an operational position of the worm wheel.

4. The remote controlled actuator assembly as claimed in claim 1, wherein the spindle guide section includes a curve portion.

* * * * *